(12) United States Patent
Sukumaran et al.

(10) Patent No.: US 11,040,946 B2
(45) Date of Patent: Jun. 22, 2021

(54) BROMONAPHTHALIMIDE COMPOUNDS AND PHOSPHORESCENT LIQUID FORMULATION THEREOF

(71) Applicant: COUNCIL OF SCIENTIFIC AND INDUSTRIAL RESEARCH, New Delhi (IN)

(72) Inventors: Santhosh Babu Sukumaran, Maharashtra (IN); Goudappagouda, Maharashtra (IN)

(73) Assignee: COUNCIL OF SCIENTIFIC AND INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 16/712,265

(22) Filed: Dec. 12, 2019

(65) Prior Publication Data

US 2021/0130298 A1  May 6, 2021

(30) Foreign Application Priority Data

Oct. 31, 2019  (IN) .............................. 201911044106

(51) Int. Cl.
*C07D 221/14* (2006.01)
*G01K 11/16* (2021.01)
*C09K 11/06* (2006.01)

(52) U.S. Cl.
CPC ............ *C07D 221/14* (2013.01); *C09K 11/06* (2013.01); *G01K 11/16* (2013.01); *C09K 2211/1018* (2013.01)

(58) Field of Classification Search
CPC ....... C07D 221/14; C09K 11/06; G01K 11/16
USPC .......................................................... 546/98
See application file for complete search history.

(56) References Cited

U.S. PATENT DOCUMENTS

2011/0042651 A1* 2/2011 Koenemann ......... C07D 221/18
257/40

OTHER PUBLICATIONS

Goudappagouda et al . Paintable Room Temperature Phosphorescent Liquid Formulations of Alkylated Bromonaphthalimide (Year: 2018).*
Goudappagouda et al . Supporting document (Year: 2018).*
Fabian Nolde et al , Synthesis and Self-Organization of Core-extended Perylene tetracarboxdiimes with branched alkyl substituents. (Year: 2006).*

* cited by examiner

*Primary Examiner* — Rita J Desai
(74) *Attorney, Agent, or Firm* — BakerHostetler

(57) ABSTRACT

The present invention provides a large scale paintable formulation of bromonapthalimide derivative compounds of formula (I) that shows phosphorescence in liquid state at 25-30° C. as well as their use as an indicator of temperature change in a visually enabled temperature measuring device.

8 Claims, 44 Drawing Sheets

BROMONAPHTHALIMIDE COMPOUNDS AND PHOSPHORESCENT LIQUID FORMULATION THEREOF

CROSS-REFERENCE TO RELATED APPLICATIONS

This application claims the benefit of priority of Indian application no. 201911044106 filed Oct. 31, 2019.

FIELD OF THE INVENTION

The present invention relates to a phosphorescent liquid formulation of bromonaphthalimide compounds and process for the preparation thereof. Particularly, the present invention relates to a large area paintable phosphorescent liquid composite with improved lifetime of a solvent-free liquid of a long swallow tailed bromonaphthalimide derivative compounds of formula (I) that exhibits phosphorescence in air. The present invention also relates to a temperature measuring device exhibiting visually enabled temperature change by using bromonapthalimide derivatives as an indicator.

BACKGROUND AND PRIOR ART OF THE INVENTION

Chemical compounds which exhibit desirable property like phosphorescence find applications in various domains. Recently, metal-free organic compounds exhibiting phosphorescence at 20-30° C. have become center of attraction for electroluminescent devices. Different functional groups like halogens, boronate ester, carbonyl group etc. play vital role in phosphorescence at 20-30° C.

Now a days, while designing organic phosphors, easy synthetic routes, air stability and structural tunability need to be considered. Hence, the incorporation of these functional moieties results in enhanced intersystem crossing with stable phosphorescence. Most of the organic phosphors reported in the prior art exhibit phosphorescence at 20-30° C. in crystalline state, than in the solution state. Crystal state phosphorescence depends on the overall organization and intermolecular interaction of the molecules in the crystal. Moreover, it reduces the triplet quenching by placing the molecules at finite distances. In addition, an efficient triplet emission is established with the help of several other methods such as matrix assisted isolation in polymers, micelles or cavitants. Hence as a successful strategy, phosphorescence in organic crystals is well exploited. Thus, organic phosphors have been mostly tested in crystalline and inert conditions, while on the other hand phosphorescent liquids have not been exploited. Therefore, organic phosphors exhibiting phosphorescence at 20-30° C. in solution or in its own liquid physical state is matter of interest.

The article titled "Synthesis and Fluorescent Property Study of Novel 1,8-Naphthalimide-Based Chemosensors" by Ying Fu 1 ID, Xiao-Xiao Pang 1, Zhi-Qiang Wang 1, Hai-Tao Qu 2 and Fei Ye 1, * published in the journal "*Molecules* 2018, 23, 376" reports synthesis of a series of novel mono- and di-substituted N-n-butyl-1,8-naphthalimide derivatives via three step reaction. The single crystal structure of N-n-butyl-4-[N',N'-bis(2',4'-dichlorobenzoyl)ethylamino]-1,8-naphthalimide (3f) is determined. The UV-vis and fluorescence properties of compound 3f are investigated.

Reference may be made to an article titled "Pendant chain engineering to fine-tune nanomorphology and solid state luminescence in naphthalimide AIEEgens: Application to phenolic nitro-explosive detection in water" by Niranjan Mehera and Parameswar Krishnan Iyer* published in the journal "*Nanoscale*, 2017, 9, 7674-7685" reports a series of five angular "V" shaped naphthalimide AIEEgens with varying pendant chains (butyl, hexyl, octyl, cyclohexyl and methylcyclohexyl) have been synthesized to fine-tune their nanomorphological and photophysical properties and process for their preparation. Alkylation on 4-bromo-1,8-naphthalic anhydride compound with alkyl amines is disclosed.

Till date, there are no reports of molecules that exhibit phosphorescence in solvent-free liquid state and its use in thermometers as a temperature change indicator. Prior arts report solids/crystals that exhibit phosphorescence, but liquid phase is more desirable, since this is easier to process application-wise. In the liquid phase molecular packing is intact, so phosphorescence is retained, unlike when solids are dissolved in solvent. When solids are dissolved in solvent, oxygen quenches and energy decay occurs very fast. Moreover, problem in the processability of crystalline phosphors also persists.

Therefore there is need to develop a new processable soft materials such as functional molecular liquid as a replacement for solid luminescent materials and process for its preparation. And it is also needed to explore the applications of such phosphorescent molecular liquid in different formulations.

OBJECTS OF THE INVENTION

Main objective of the present invention is to provide bromonapthalimide compounds of formula (I) that show phosphorescence in solid and solvent-free liquid state and process for the preparation thereof.

Another objective of the present invention is to provide formulation comprising bromonapthalimide compounds of formula (I) with fillers, additives, polymers, reinforcements, wherein the formulation displays solvent free liquid state phosphorescence. Yet another objective of the present invention is to provide a paintable phosphorescent liquid composite with enhanced luminescent quantum yield and lifetime.

Yet another objective of the present invention is to provide temperature measuring device comprising bromonapthalimide derivative compounds of formula (I) that shows phosphorescence in solid and solvent-free liquid state.

SUMMARY OF THE INVENTION

Accordingly, present invention provides a compound of formula 1(e)

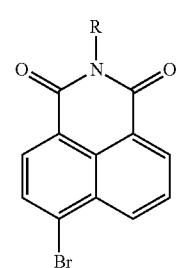

Formula 1(e)

[6-bromo-2-(tricosan-12-yl)-1H-benzo[de]isoquinoline-1,3(2H)-dione]

wherein R=

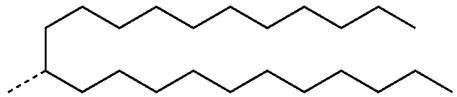

In an embodiment, present invention provides a process for the preparation of compound of formula 1(e) comprising the steps of.

i) charging compound 6-bromo-1H,3H-benzo[de]isochromene-1,3-dione of formula 1, pentacosan-13-amine in alcohol solvent to obtain a reaction mass;

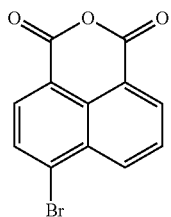

Formula 1 ii) heating the reaction mass as obtained in step (i) at temperature in the range of 70-160° C. followed by maintaining the reaction mixture at 70-160° C. preferably at 160° C. for period in the range of 8-15 hr preferably for 8 hr under argon atmosphere to obtain a reaction mass;

iii) cooling the reaction mass as obtained in step (ii) at temperature in the range of 20-30° C. followed by filtering and washing with water to obtain a solid; iv) drying the solid as obtained in step (iii) under vacuum to afford compound of formula (1e).

In another embodiment of the present invention, the said alcohol solvent is selected from the group consisting of methanol, ethanol, isopropyl alcohol, n-propanol, n-butanol, ethylene glycol and mixtures thereof preferably ethylene glycol.

In yet another embodiment of the present invention, said compound exhibits liquid state phosphorescence at 20-30° C. in air.

In yet another embodiment, present invention provides a paintable formulation exhibiting phosphorescence at 20-30° C. in neat form comprising compound of formula 1(e).

1. In yet another embodiment of the present invention, the paintable formulation further comprises of doping with carbonyl groups.
2. In yet another embodiment of the present invention, the said carbonyl groups are introduced with the compounds benzene-1,3,5-tricarbaldehyde and terephthalaldehyde.
3. In yet another embodiment, present invention provides a temperature measuring visual device comprising compound of formula I wherein the range of temperature measured is −196° C. to 25° C. with a colour change.

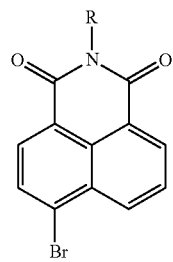

Formula (I)

wherein R is selected from straight or branched $C_1$ to $C_{50}$ alkyl group.

DETAILED DESCRIPTION OF THE INVENTION

Figure 1A:
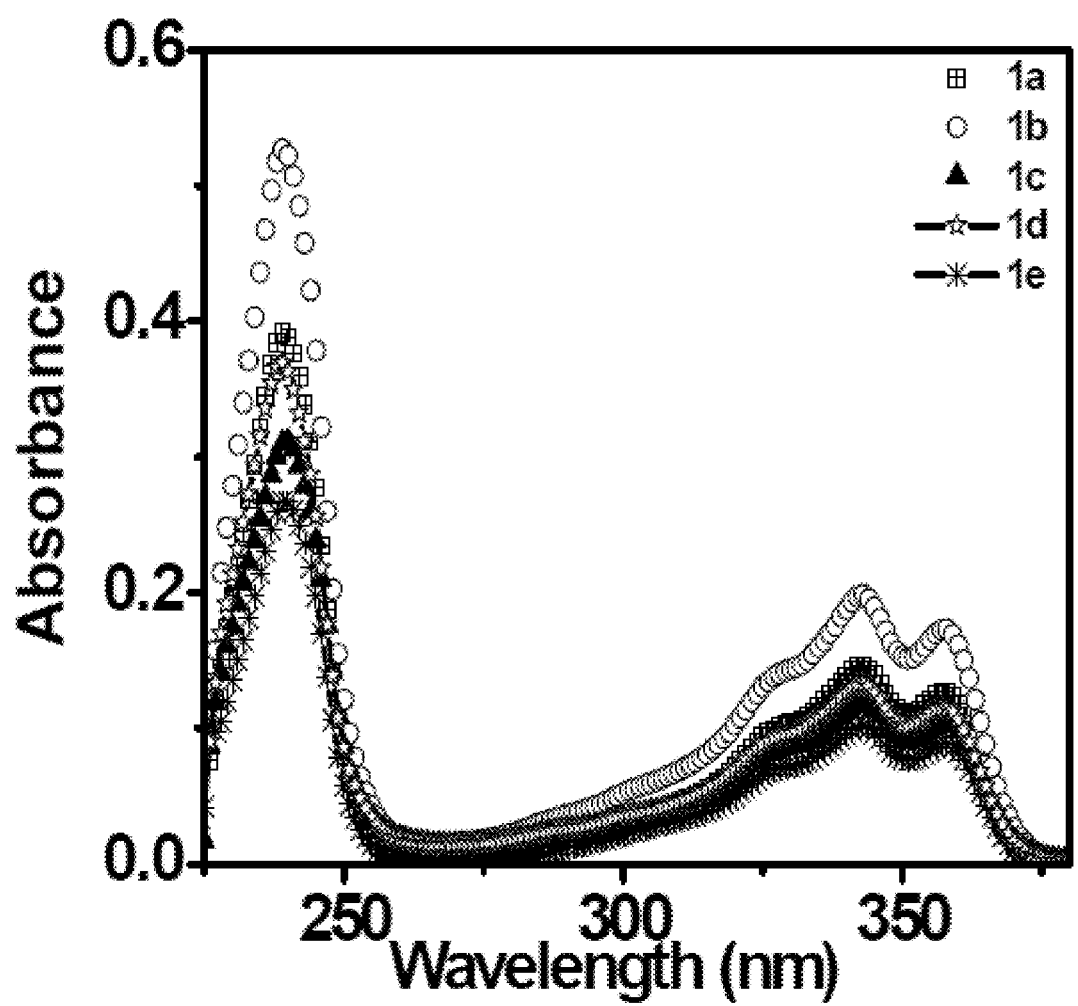
FIGS. 1A-B represent (a) Absorption and (b) emission spectra of compounds of formulae 1a-e DCM solution ($\lambda_{ex}$=342 nm, C=1×10$^{-5}$ M, l=1 cm).

Present invention provides a bromonapthalimide derivative compound of formula (I) that show phosphorescence in solid and solvent-free liquid state.

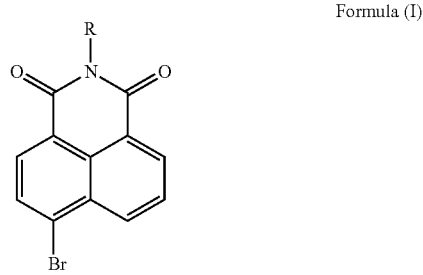

Formula (I)

wherein, R is selected from straight or branched $C_1$ to $C_{50}$ alkyl group.

The 4-bromo-1,8-naphthalimide compounds of formula (I) is selected from 6-bromo-2-butyl-1H-benzo[de]isoquinoline-1,3(2H)-dione (1a), 6-bromo-2-octyl-1H-benzo [de]isoquinoline-1, 3(2H)-dione (1b), 6-bromo-2-dodecyl-1H-benzo[de]isoquinoline-1,3(2H)-dione (1c), 6-bromo-2-(2-ethylhexyl)-1H-benzo[de]isoquinoline-1,3(2H)-dione (1d) or 6-bromo-2-(tricosan-12-yl)-1H-benzo[de]isoquinoline-1, 3(2H)-dione (1e).

Present invention provides formulation comprising new bromonapthalimide derivative compounds of formula (I) with fillers, additives, polymers, reinforcements, wherein the product or formulation displays solvent free liquid state phosphorescence. More particularly, the present invention relates to a large area paintable phosphorescent liquid composite with improved lifetime of a solvent-free liquid of a long swallow tailed bromonaphthalimide derivative compounds of formula (I) that exhibits phosphorescence at 20-30° C. in air. Doping of the phosphor with carbonyl groups resulted in enhanced phosphorescence and hence a large area paintable phosphorescent liquid composite with improved lifetime and quantum yield is developed. A relatively large area (10×10 cm2) phosphorescent composite coating at 20-30° C. is realised by using the liquid composite paint.

The present invention provides a formulation comprising a compound, 6-bromo-2-(tricosan-12-yl)-1H-benzo[de]isoquinoline-1,3(2H)-dione of formula (1e) with fillers, additives, polymers, reinforcements, wherein the product or formulation displays solvent free liquid state phosphorescence.

The present invention provides a temperature measuring device that exhibits visually enabled temperature change by colour tenability from green to orange comprising of a 4-bromo-1,8-naphthalimide derivative compounds of formula (I) that show phosphorescence in solid and solvent-free liquid state and indicate changes in temperature by colour tenability from green to orange.

Figure 19:
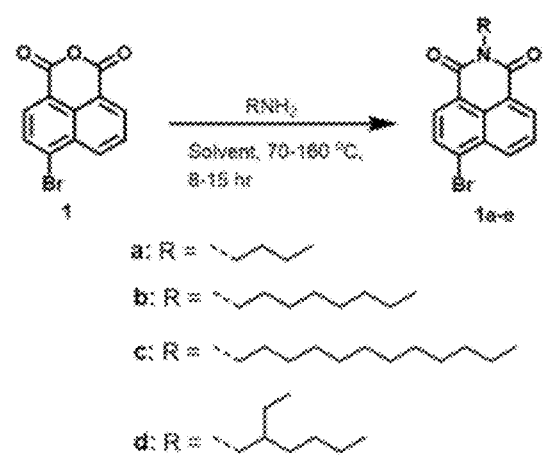
FIG. 19 represents process step for the preparation of compound of formula 1a-e.

The present invention provides process for the preparation of 4-bromo-1,8-naphthalimide derivative compounds formula (I) comprises heating the reaction mixture of alkylamine with compound of formula 1 in solvent at a temperature in the range of 70 and 160° C. for a period in the range of 6 to 15 hrs to afford 4-bromo-1,8-naphthalimide compound formula (I). The process is depicted in FIG. 19.

Figure 20:
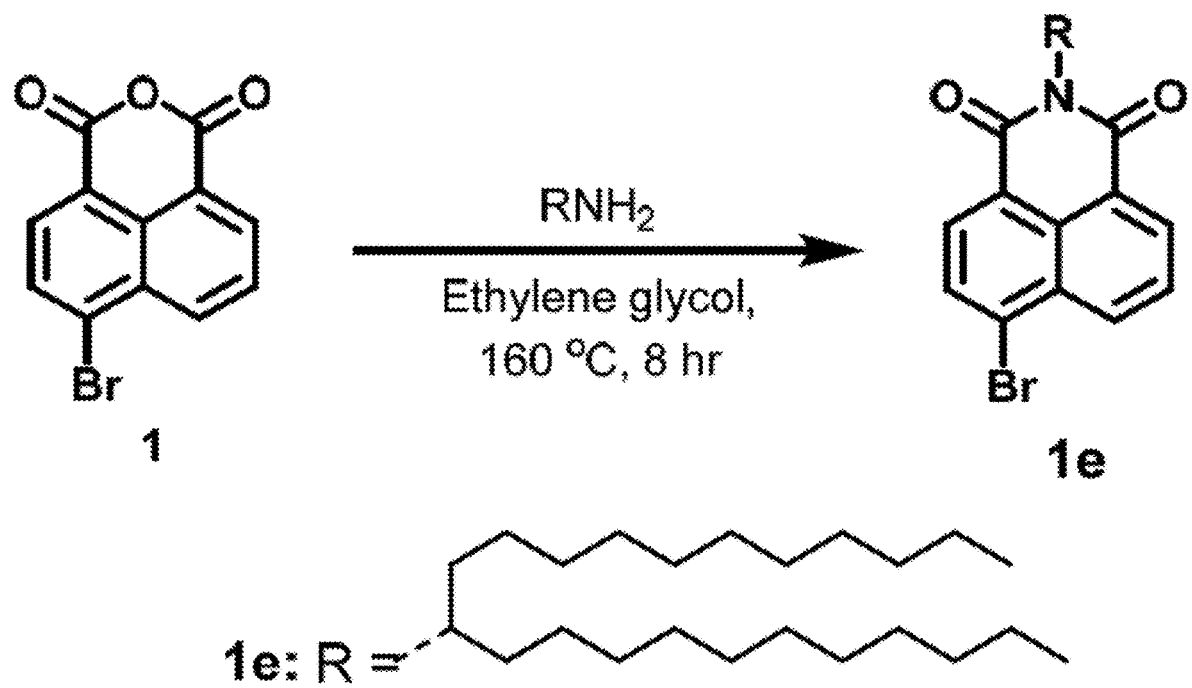
FIG. 20 represents process for the preparation of compound, 6-bromo-2-(tricosan-12-yl)-1H-benzo[de]isoquinoline-1,3(2H)-dione of formula (1e).

The present invention provides process for the preparation of compound, 6-bromo-2-(tricosan-12-yl)-1H-benzo[de]isoquinoline-1,3(2H)-dione of formula (1e), as depicted in FIG. 20.

The process for the preparation of compound, 6-bromo-2-(tricosan-12-yl)-1H-benzo[de]isoquinoline-1,3(2H)-dione of formula (1e), comprises of following steps:
i) charging compound, 6-bromo-1H,3H-benzo[de]isochromene-1,3-dione of formula 1, pentacosan-13-amine in suitable solvent;
ii) heating the reaction mass from step i) to suitable temperature;
iii) maintaining the reaction mixture from step ii) at 160° C. for suitable period of time under argon atmosphere;
iv) cooling the reaction mass from step iii) to 20-30° C.;
v) filtering and washing the obtained solid with water; and
vi) drying the obtained solid from step v) under vacuum to afford compound of formula 1e.

Suitable solvent used at step i) may include alcohol solvent, polar solvent, ether solvent, ester solvent, and mixtures thereof. Alcohol solvent may include methanol, ethanol, isopropyl alcohol, n-propanol, n-butanol, ethylene glycol and mixtures thereof. Polar solvent may include water, acetone, ammonia, sulfuric acid, deuterium oxide, acetone, methyl ethyl ketone, n-propanol, acetonitrile, DMSO, and DMF and mixtures thereof. Ether solvent may include tetrahydrofuran, diethyl ether, 1,4-dioxane, methyl tert-butyl ether, and mixtures thereof. Ester solvent may include methyl acetate, ethyl acetate, isopropyl acetate, tert-butyl acetate, and mixtures thereof. In particularly useful embodiments, alcohol solvent is used and most preferably ethylene glycol is used as a solvent in step i).

Suitable temperature range at step ii) is 70-160° C., and in particularly useful embodiment, most preferably 160° C.

Suitable period of time to maintain the reaction mass at step iii) is for 8-15 hr, and in particularly useful embodiment, most preferably 8 hr.

Figure 1B:
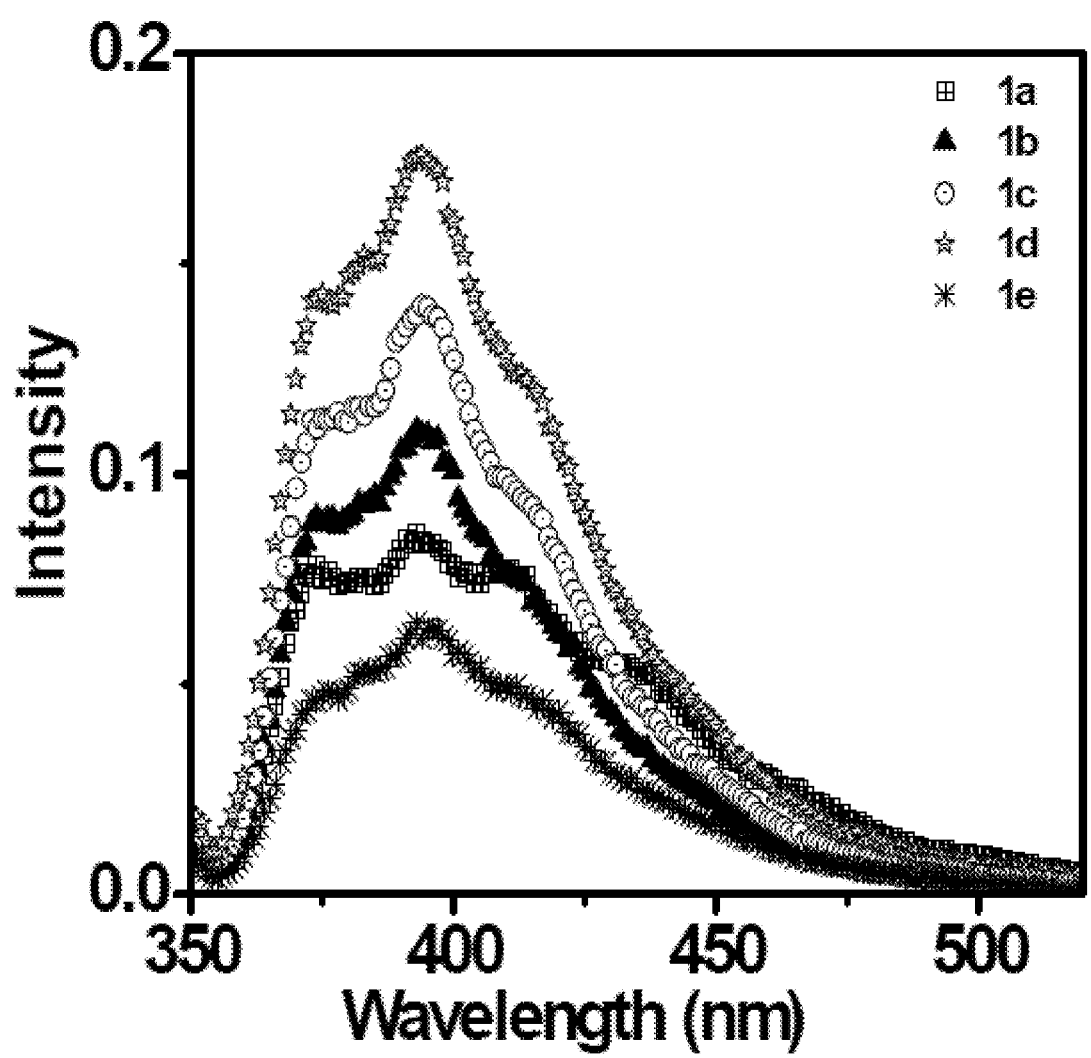

The absorption spectrum of compounds of formula (I), more specifically compounds of formula 1a-e is recorded in dichloromethane (DCM) solution. Compounds of formulae 1a-1e exhibit absorption characteristics in the UV region with max of 239 nm as shown in FIG. 1B and at longer wavelength region with $\lambda_{max}$ of 342 nm and 357 nm, which extend to visible region and corresponds to π-π* transition.

Figure 2A:
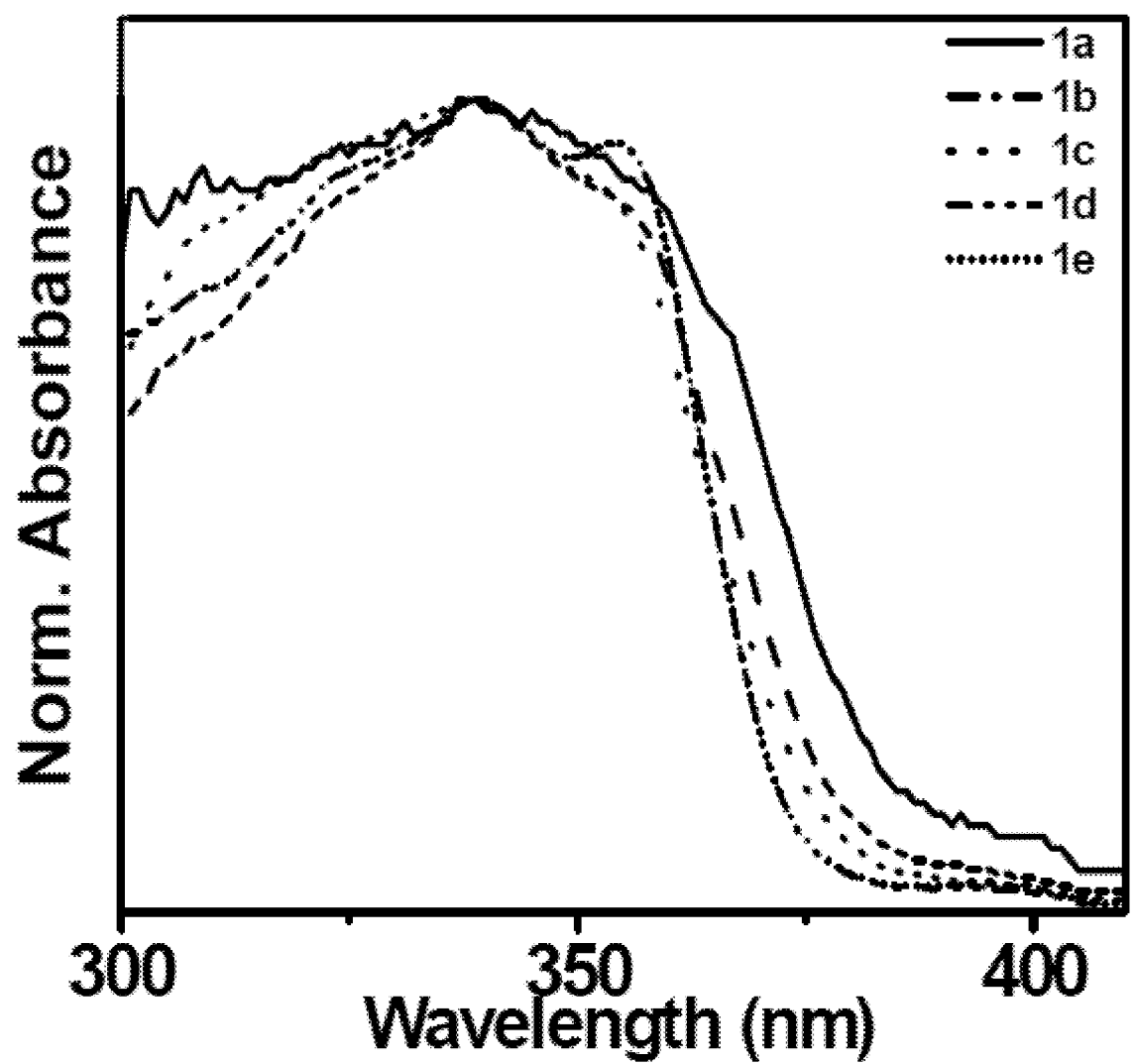
FIGS. 2A-B represent (a) Absorption and (b) emission spectra of compounds of formulae 1a-e thin film ($\lambda_{ex}$=342 nm, C=1×10$^{-5}$ M, l=1 cm).
Figure 2B:
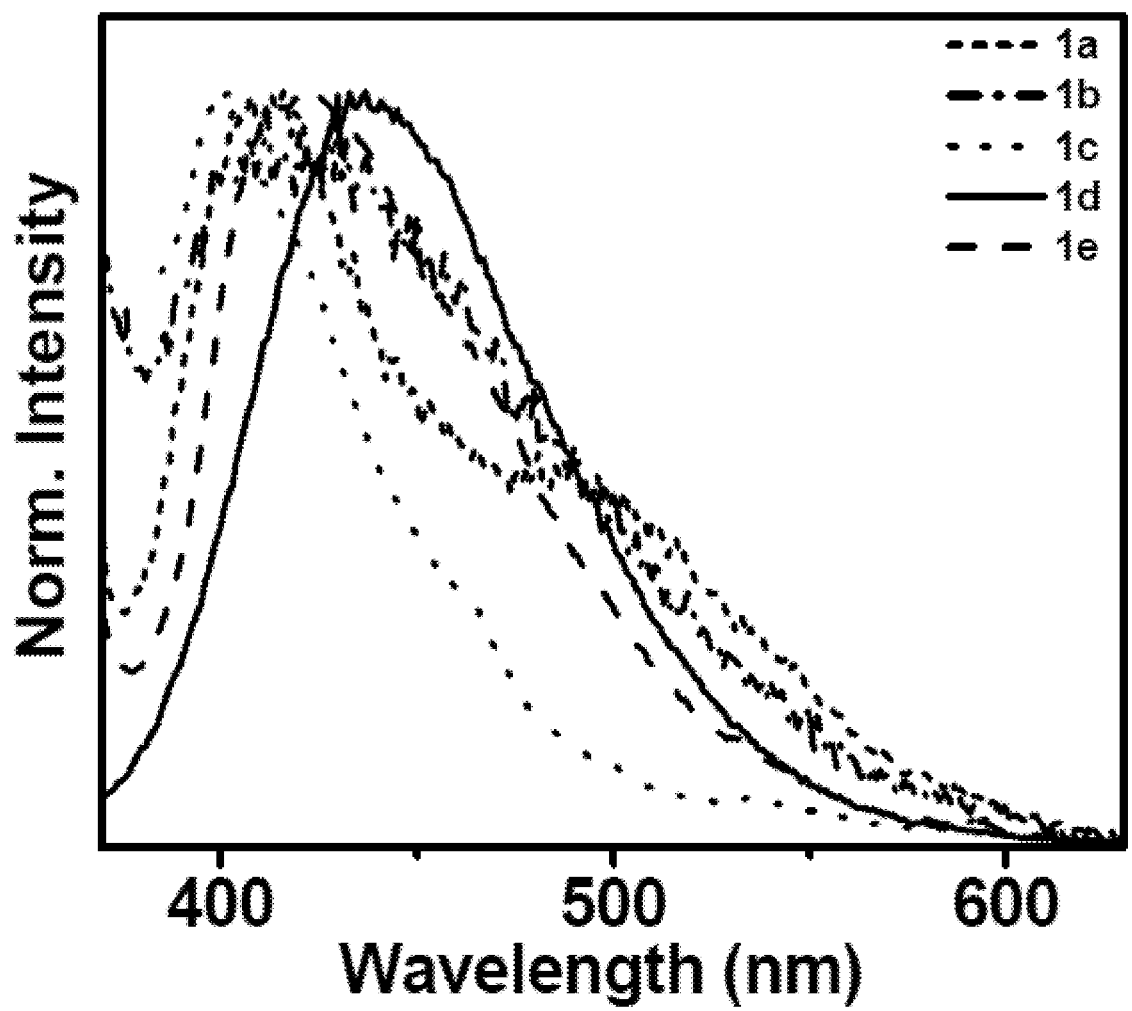
Figure 3A:
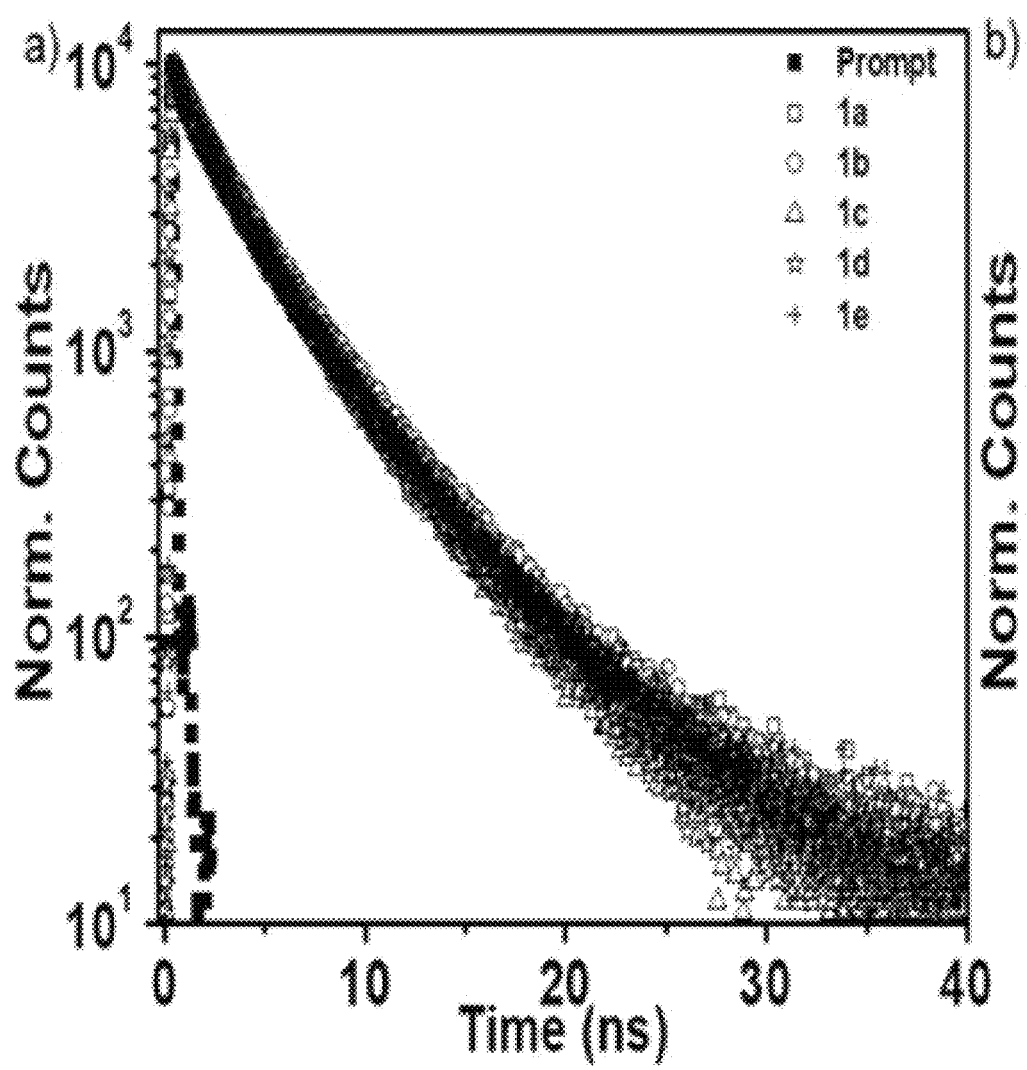
FIGS. 3A-B represent emission lifetime decay profile of compounds of formulae 1a-e in (a) DCM solution (C=1×10$^{-5}$ M, l=1 cm, λex=374 nm, λmon=395 nm) and (b) thin film (λex=374 nm, λmon=395 nm).
Figure 3B:
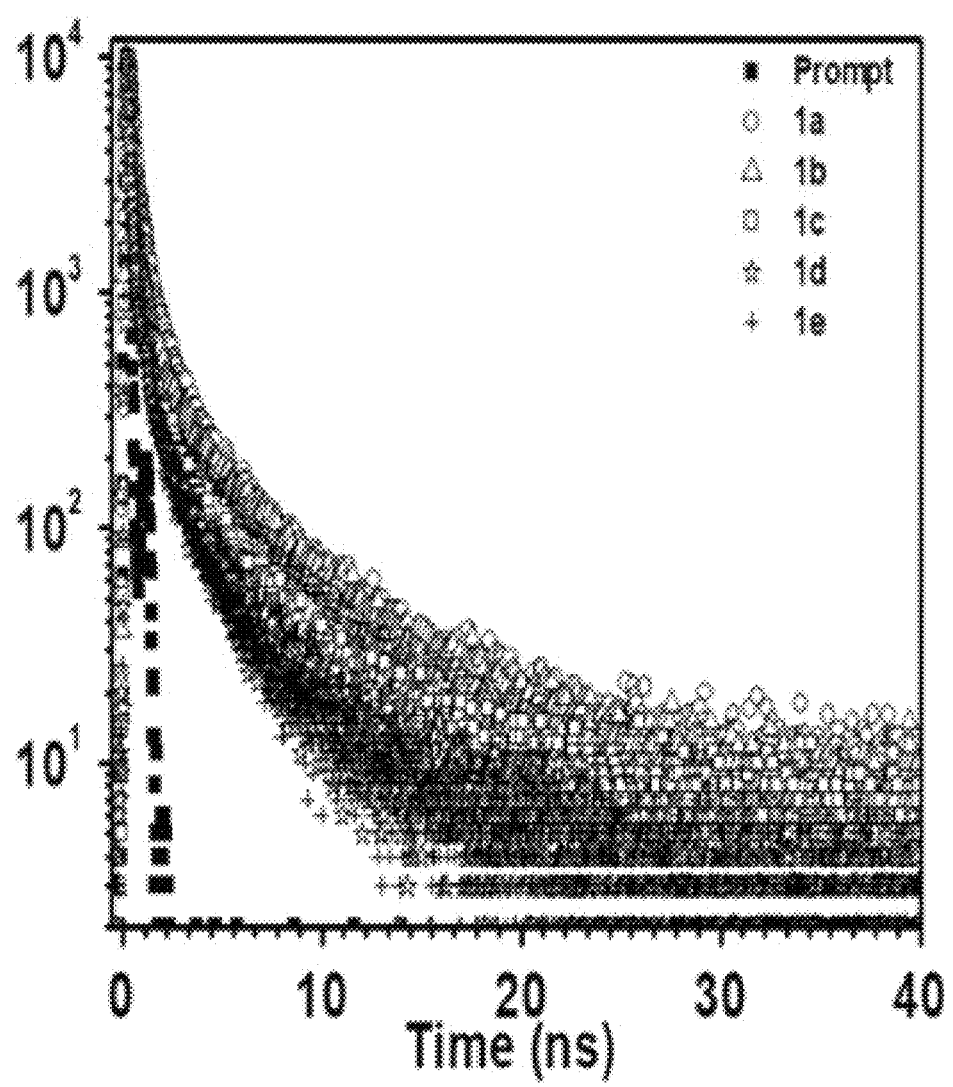

Steady-state emission spectra are also recorded in dichloromethane (DCM). In solution state, when 1a-e are excited at 342 nm, emission spectra with $\lambda_{max}$ of 395 nm and shoulder band at 415 nm is observed as shown in FIGS. 1A and 1B. Thin films of compounds of formulae 1a-1e displayed broad UV-Vis spectrum with a considerable red shift. Solvent-free liquid compound of formula 1e has a broad spectrum with maximum located at 430 nm, as shown in FIG. 2A. Emission spectra of 1a-1e will come in the range of 350 nm to 600 nm (FIG. 2B). Fluorescence lifetime decay measurements in dichloromethane (DCM) solution and thin film of compounds of formulae 1a-1e exhibited a biexponential decay due to possible intermolecular interactions, as shown in FIGS. 3A-B. The fluorescence lifetimes with corresponding population of all compounds (1a-1e) in dichloromethane (DCM) solution and thin film are given in Table 1, and 2, respectively.

TABLE 1

Comparison of the emission lifetime of 1a-e in DCM solution ($\lambda$ex = 374 nm, $\lambda$mon =395 nm).

| SI No | Sample Name | Lifetime |
|---|---|---|
| 1 | 1a | T1 = 2.86 ns (33.24%) |
|   |    | T2 = 7.61 ns (66.74%) |
| 2 | 1b | T1 = 2.07 ns (39.00%) |
|   |    | T2 = 5.36 ns (61.00%) |
| 3 | 1c | T1 = 2.00 ns (40.72%) |
|   |    | T2 = 4.97 ns (59.28%) |
| 4 | 1d | T1 = 1.80 ns (33.40%) |
|   |    | T2 = 5.10 ns (66.60%) |
| 5 | 1e | T1 = 1.79 ns (34.15%) |
|   |    | T2 = 5.14 ns (65.85%) |

TABLE 2

Comparison of the emission lifetime of 1a-e in thin film ($\lambda$ex = 374 nm).

| SI No | Sample Name | Lifetime |
|---|---|---|
| 1 | 1a | T1 = 0.25 ns (19.95%) |
|   |    | T2 = 1.38 ns (28.37%) |
|   |    | T2 = 6.03 ns (51.68%) |
| 2 | 1b | T1 = 0.02 ns (9.61%) |
|   |    | T2 = 0.57 ns (14.17%) |
|   |    | T2 = 4.96 ns (76.22%) |
| 3 | 1c | T1 = 0.01 ns (10.20%) |
|   |    | T2 = 0.58 ns (11.57%) |
|   |    | T2 = 4.14 ns (78.28%) |
| 4 | 1d | T1 = 0.02 ns (14.90%) |
|   |    | T2 = 0.31 ns (18.91%) |
|   |    | T2 = 3.36 ns (66.20%) |
| 5 | 1e | T1 = 0.12 ns (11.73%) |
|   |    | T2 = 0.80 ns (21.87%) |
|   |    | T2 = 4.34 ns (66.40%) |

Figure 4:
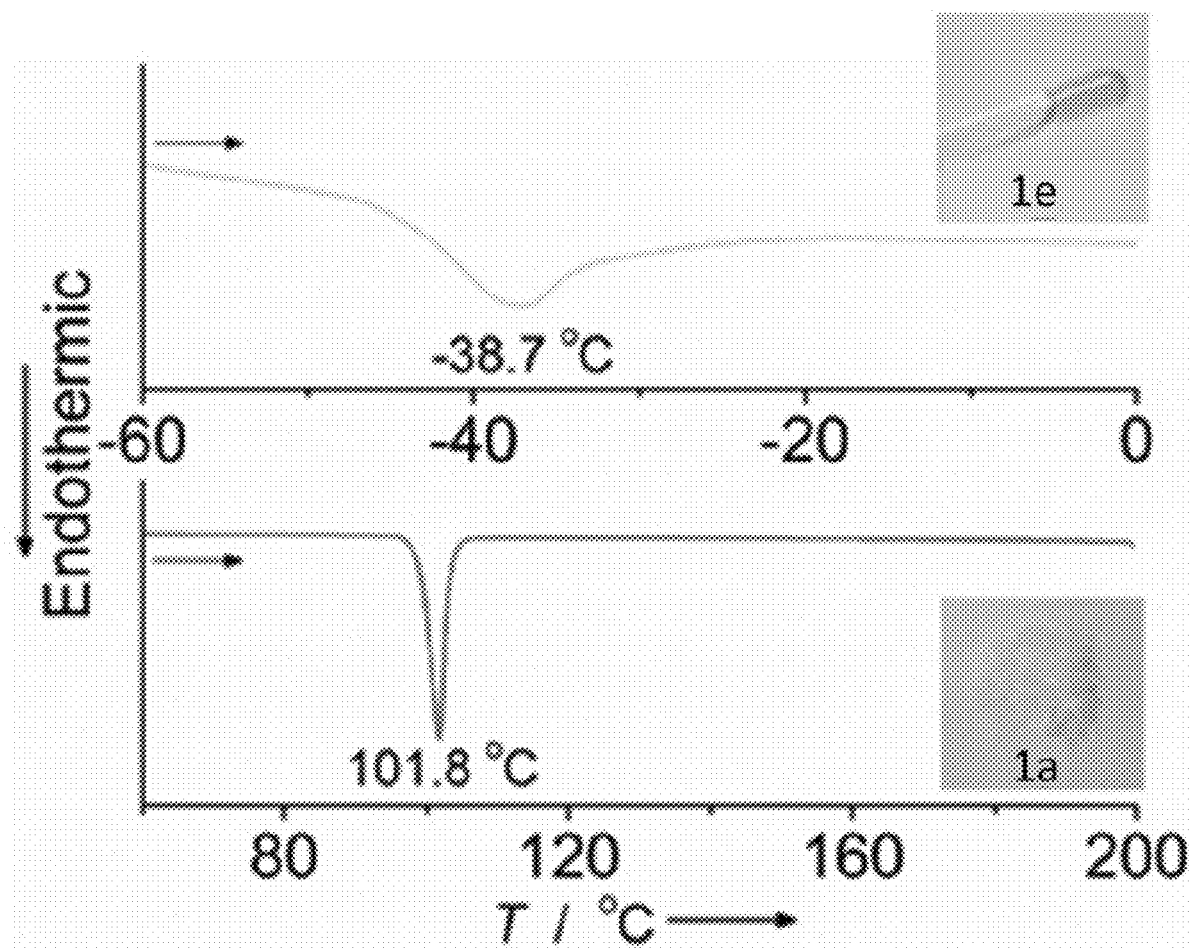
FIG. 4 represents DSC thermograms of compounds of formulae 1a and 1e in the heating trace at a scanning rate of 10° C./min; insets show the photographs of 1a and 1e, respectively.
Figure 5:
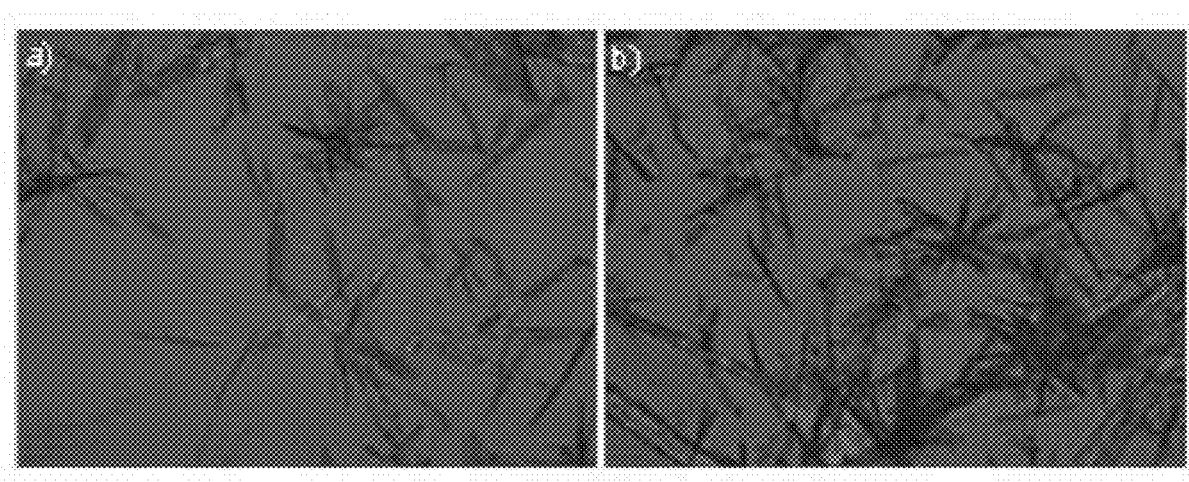
FIG. 5 represents optical microscope images of compound of formula 1a crystals drop casted on silicon.
Figure 6:
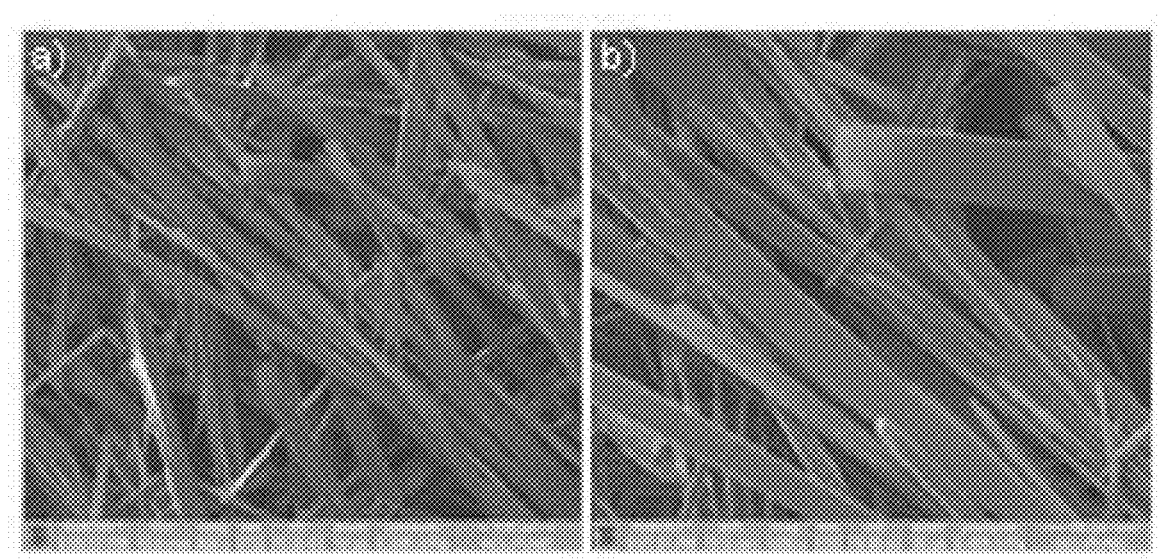
FIG. 6 represents SEM images of compound of formula 1a crystals drop casted on silicon.
Figure 8:
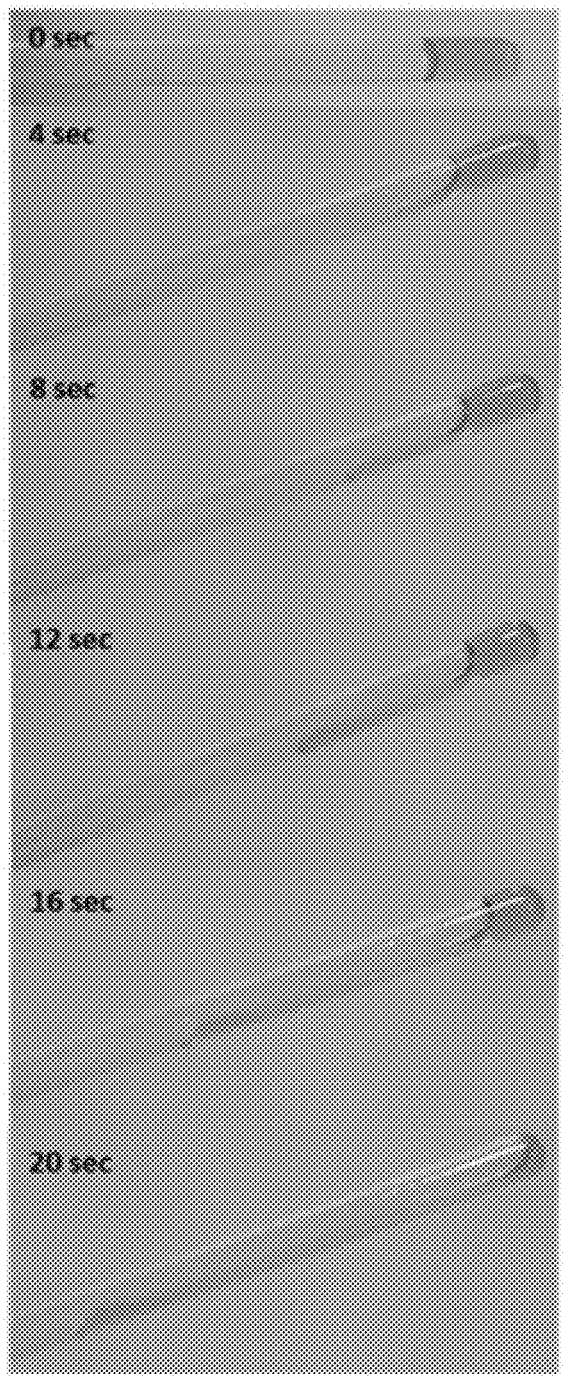
FIG. 8 represents photograph of compound of formula 1e showing the free-flowing liquid feature.
Figure 9:
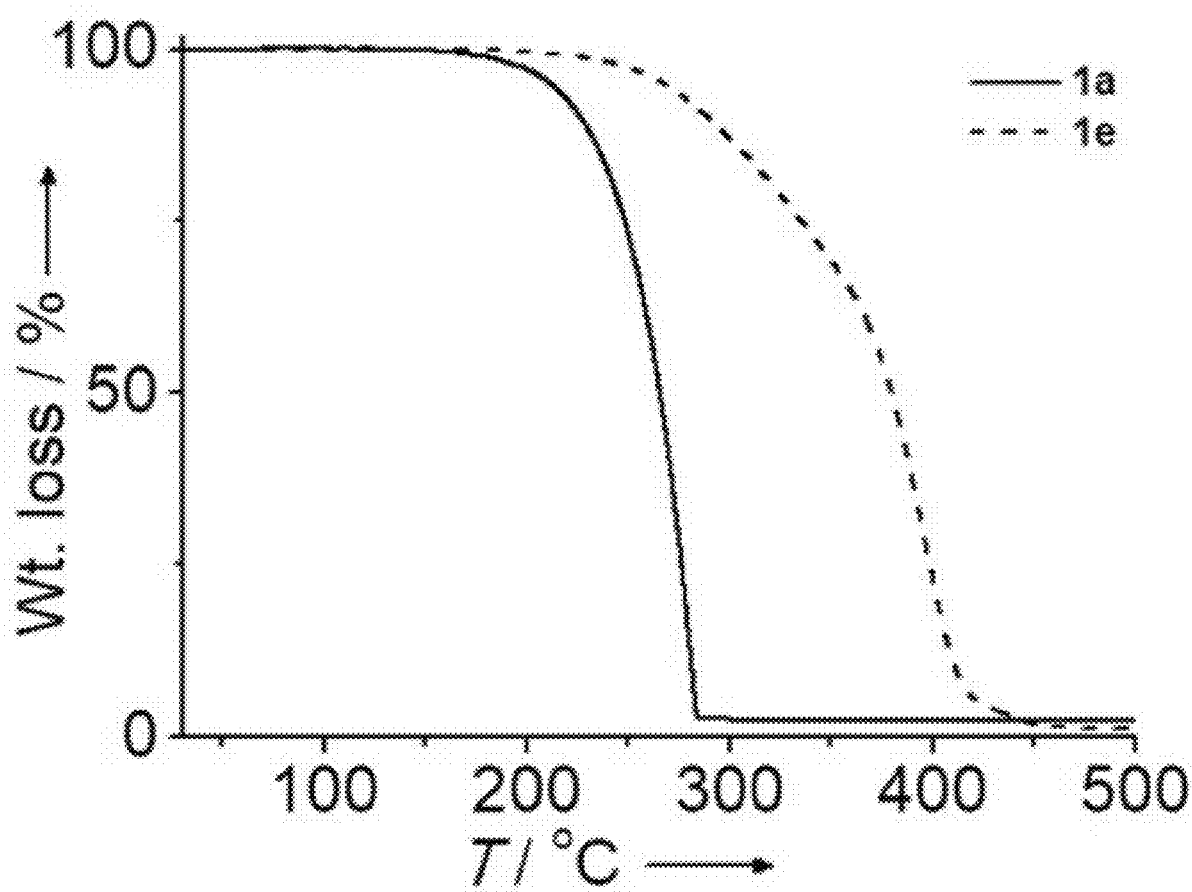
FIG. 9 represents thermogravimetric analysis of compounds of formulae 1a and 1e.

The phase transition temperatures of compounds of formulae 1a-1e are determined by differential scanning calorimetry (DSC), as shown in FIG. 4. Compound of formula 1e show glassy transition temperature at −40.56° C. (Tg) which is different from the high melting points of crystals of compounds 1a-1d (68.3-101.8° C. (Tm)). This trend is clearly visible in the physical appearance of compounds of formulae 1a-1e, as depicted in FIGS. 5-8. The high melting point of compound of formula 1a and low phase transition temperatures of compound of formula 1e, together with their thermal stabilities as indicated by TGA as shown in FIG. 9, allow compounds of formulae 1a and 1e to exist as crystal, as shown in FIGS. 7A-C and solvent-free liquid as shown in FIG. 8, respectively, over a range of temperature.

Figure 7A:
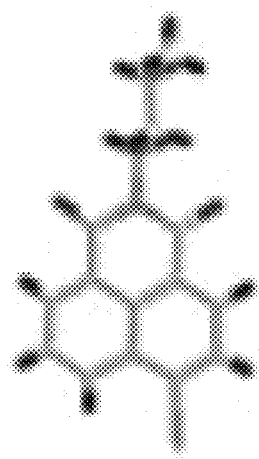
FIGS. 7A-C represent crystal structure of compound of formula 1a showing (a) single molecule, (b) unit cell and (c) extended molecular packing.
Figure 7B:
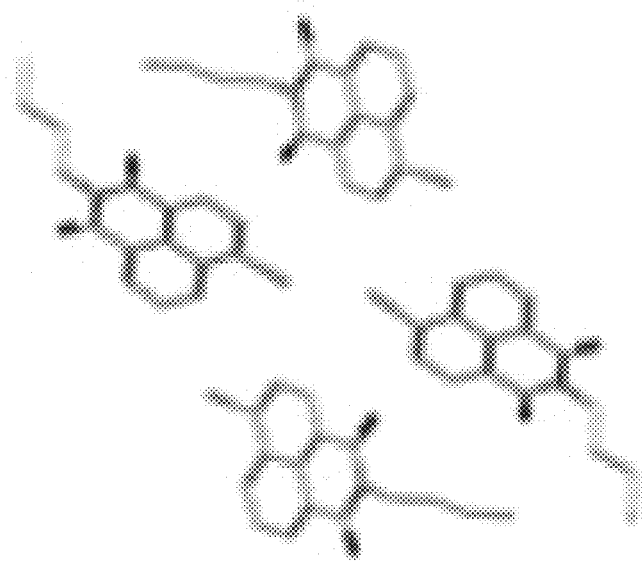
Figure 7C:
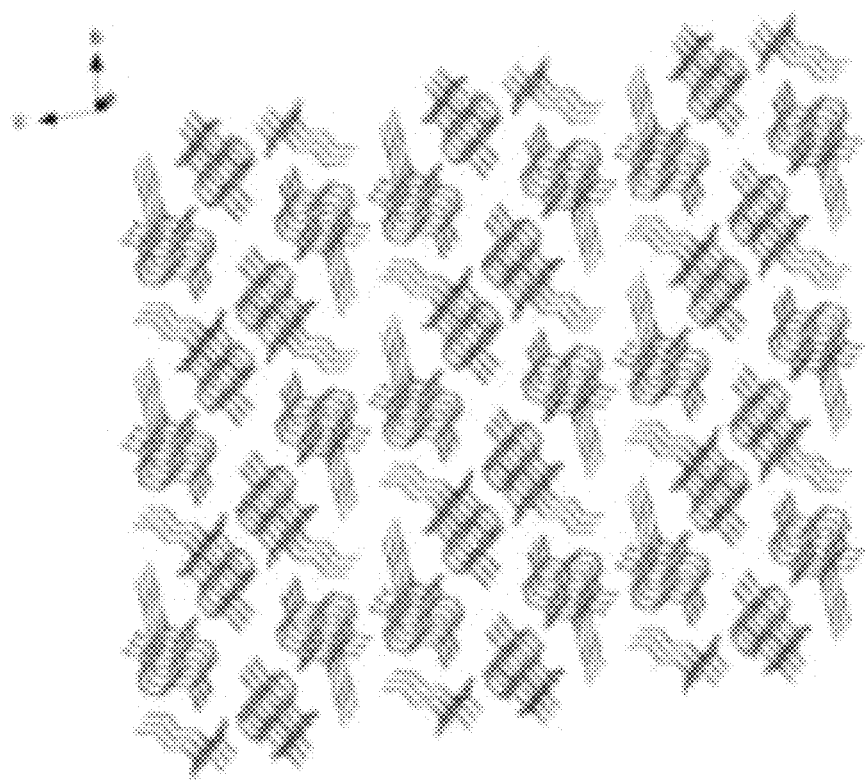

Single crystal X-ray analysis enables to study the molecular arrangements of 1, which crystallizes from ethanol in the triclinic space group P-1 (CCDC: 1873219) (FIG. 7A). A unit cell consists of four molecules of 1 bound together by C=O • • • H—C(Ar) hydrogen bonding (3.2 Å), Br • • • Br interaction (4.4 Å) and van der Walls interactions of the alkyl chains (FIG. 7B). An extended arrangement along a-axis found possible using the advantage of 1-1 stacking (4.4 Å), Br • • • Br interaction (4.4 Å) and van der Walls interactions (FIG. 7C). Unit cells pack along b-axis using Br • • • O halogen bonding (4.8 Å). The columns of 1 form a further extended packing along c axis guided by strong C=O• • • H—C hydrogen bonding and van der Walls interactions.

The direct effect of alkyl modification in tuning the physical characteristics of molecules. As a result, 1 form needle-like crystal and 2 stays as RT liquid upon evaporation from CH2Cl2 solution (FIGS. 6 and 8).

Figure 10:
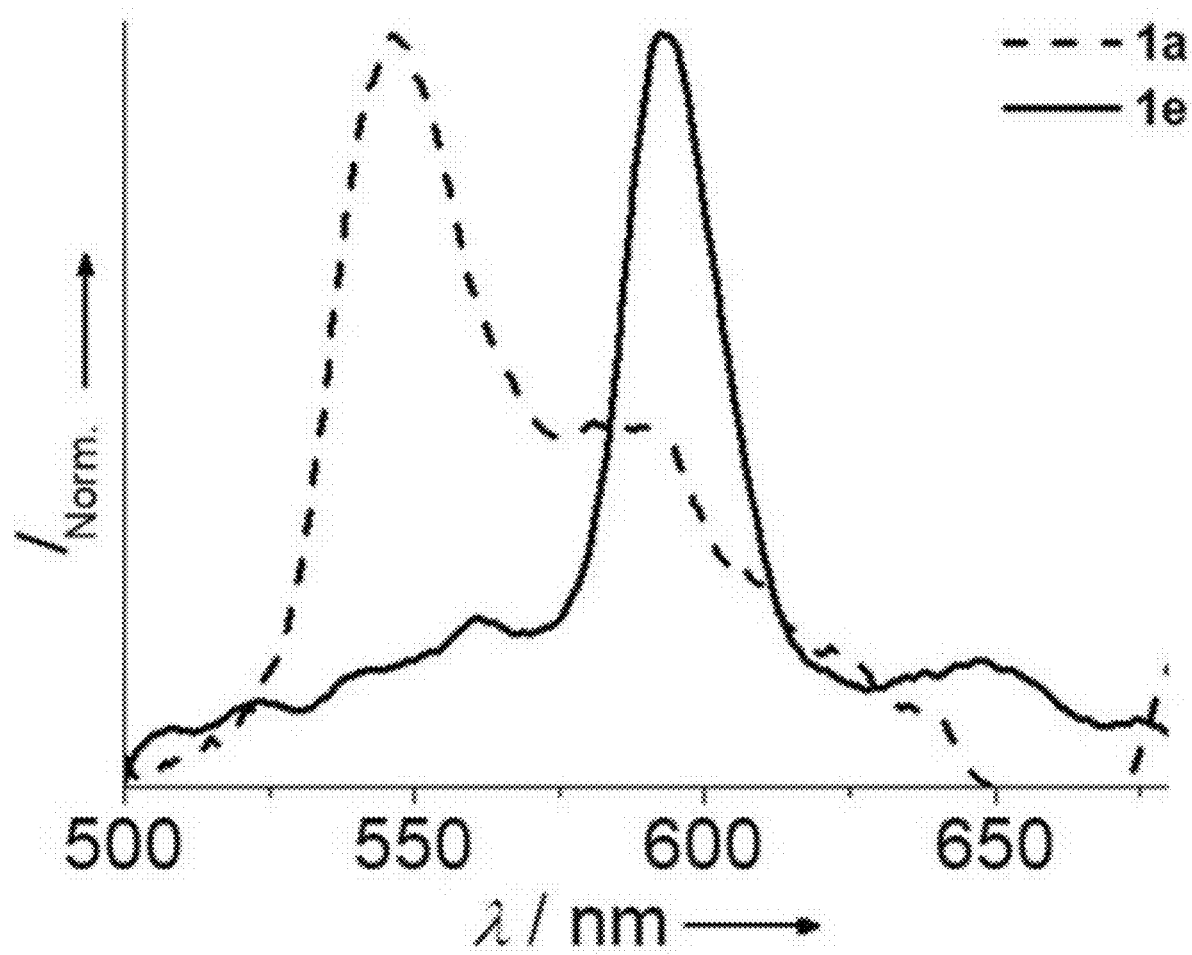
FIG. 10 represents normalized phosphorescence spectra of solid compound of formula 1a and solvent-free liquid compound of formula 1e at 25° C. in air ($\lambda_{ex}$=345 nm).

As part of characterization, the phosphorescence of compounds of formulae 1a-1e in 2-methyltetrahydrofuran (MTHF) solution (77k) as well as in neat (RT) is studied and it is observed that all derivatives are phosphorescence active as shown in FIG. 10 and exhibit two peaks in the phosphorescence spectra. When compounds of formulae 1a-1e in solution state (77k) are excited at 342 nm, a phosphorescence emission spectra with $\lambda_{max}$ of 540 nm and 590 nm, respectively, is observed. At lower temperature, except compounds of formulae 1b and 1c, all other derivatives showed a red shifted emission. It is observed in most of the phosphors that at low temperature a red shifted emission peak is present.

Figure 11A:
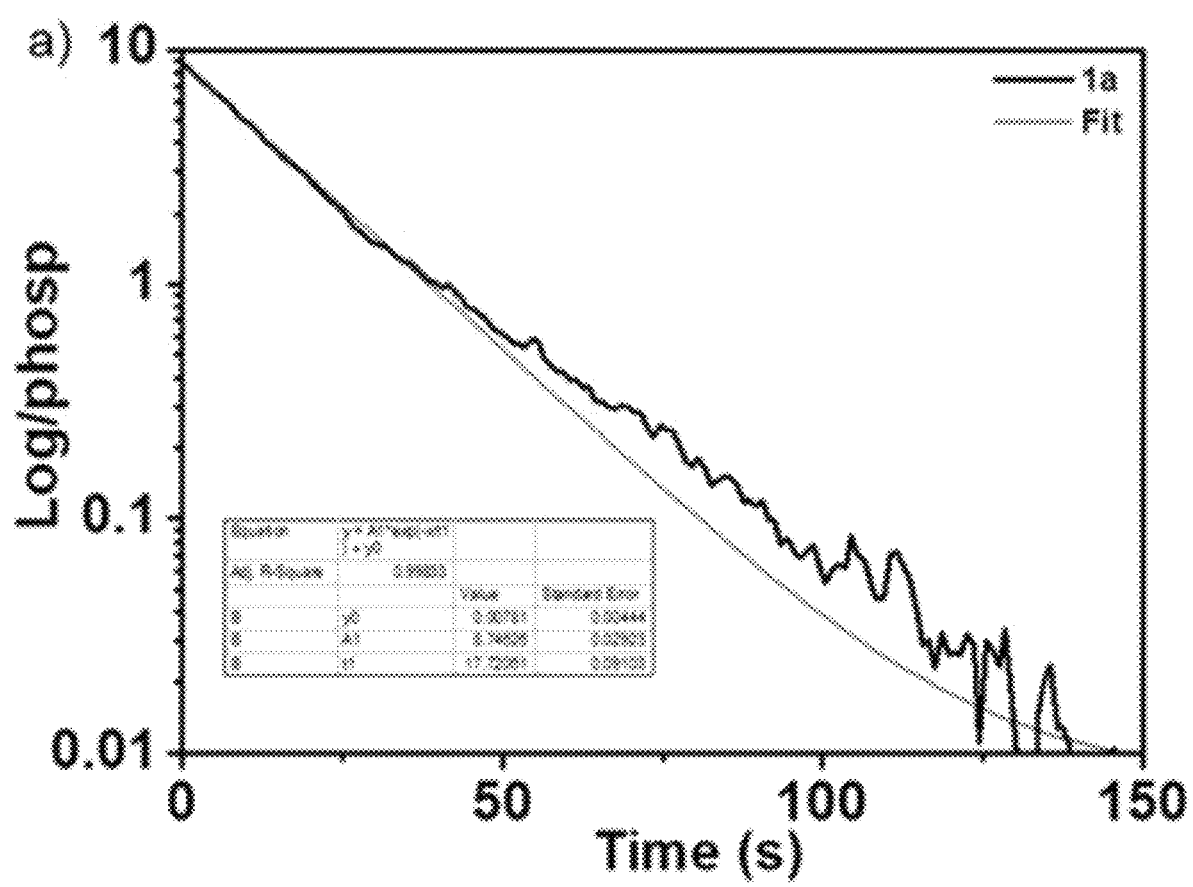
FIGS. 11A-B represent phosphorescence lifetime decay profile of neat of compounds of formulae 1a (a) and 1e (b) recorded in air at 30° C. ($\lambda_{ex}$=355 nm).
Figure 11B:
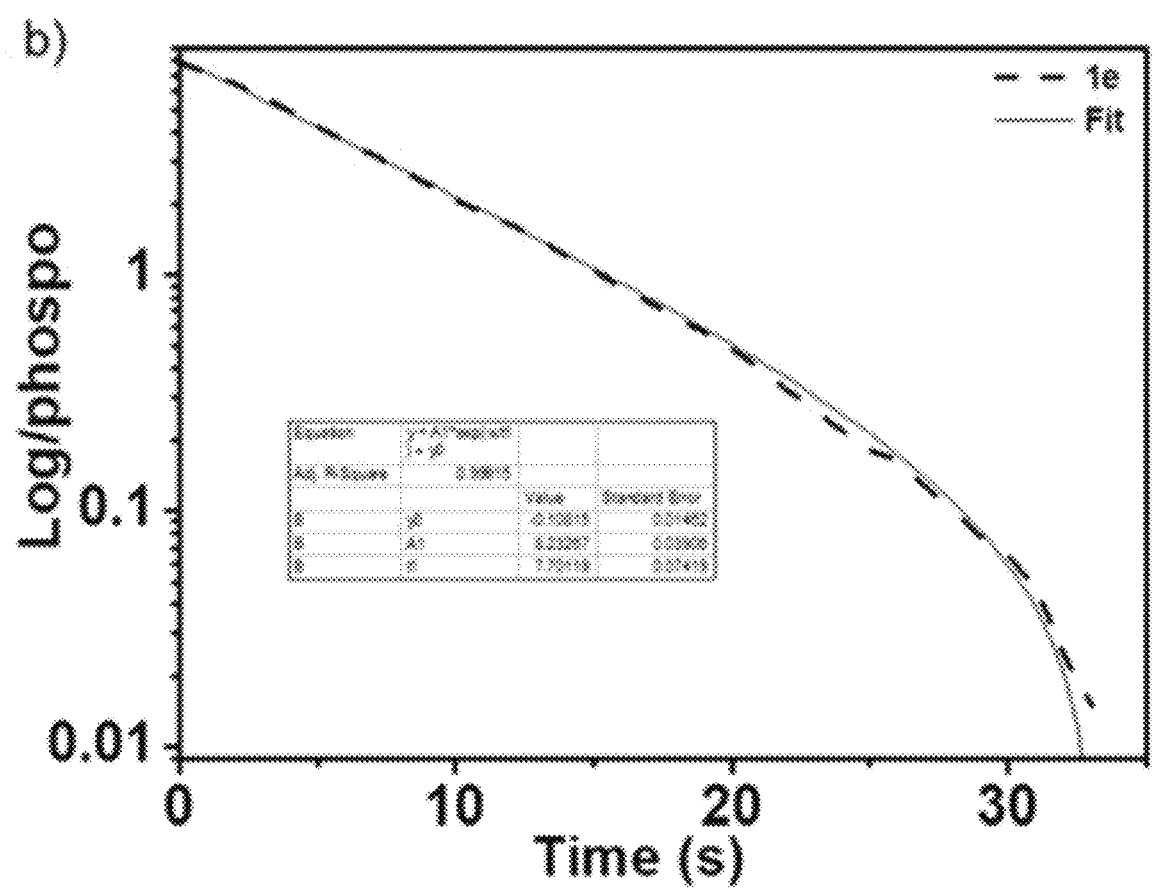

The photographs of compounds of formulae 1a-1e show the phosphorescence after dipping the 2-methyltetrahydrofuran (MTHF) solution in liquid nitrogen (3 sec) and after switching off UV light (365 nm) used for exciting the samples (2 sec). When compounds of formulae 1a-1e (neat at RT) are excited at 345 nm, phosphorescence spectra exhibited $\lambda_{max}$ of 589 nm, 593 nm, 578 nm, 603 nm, 594 nm, respectively. Compounds of formulae 1d and 1e showed a red shifted peak at 20-30° C. in comparison with compounds of formulae 1a-1c. Phosphorescence lifetimes of compounds of formulae 1a and 1e are found to be 6.2, 5.7 ms at 30° C., as shown in FIGS. 11A-B.

In an aspect of the invention, the crystallisation of compound 1b-d resulted in the formation of noncrystalline aggregates, while compound 1e remained as free flowing liquid at 20-30° C. Further, compounds 1a-e exhibited temperature dependent tunable emission features.

In another aspect of the invention, a thermometer comprising the 4-bromo-1,8-naphthalimide compound of formula (I) substituted with a temperature range of 30° C. to −196° C. by colour tunability from green to orange, wherein the thermometer detects changes in temperature by colour change that can be detected visually.

Figure 12A:
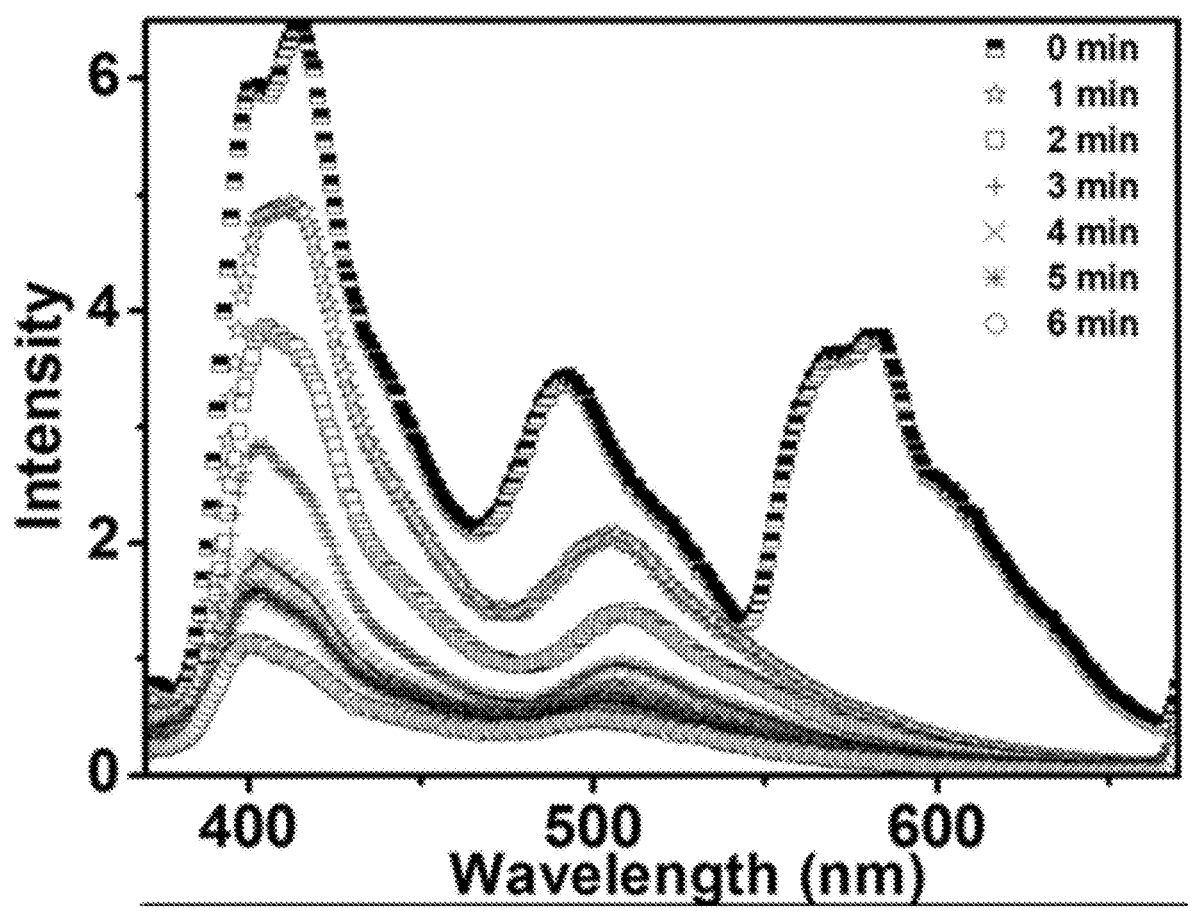
FIGS. 12A-C represent (a) Time temperature dependent tunable emission spectral changes of compound of formula 1a after dipping the solution in liquid $N_2$ (b) Temperature dependent tunable emission spectral changes of compound of formula 1a with (c) corresponding photographs showing reversible tunable emission colours; blue at 25° C., green at −110° C. and red at −196° C.
Figure 12B:
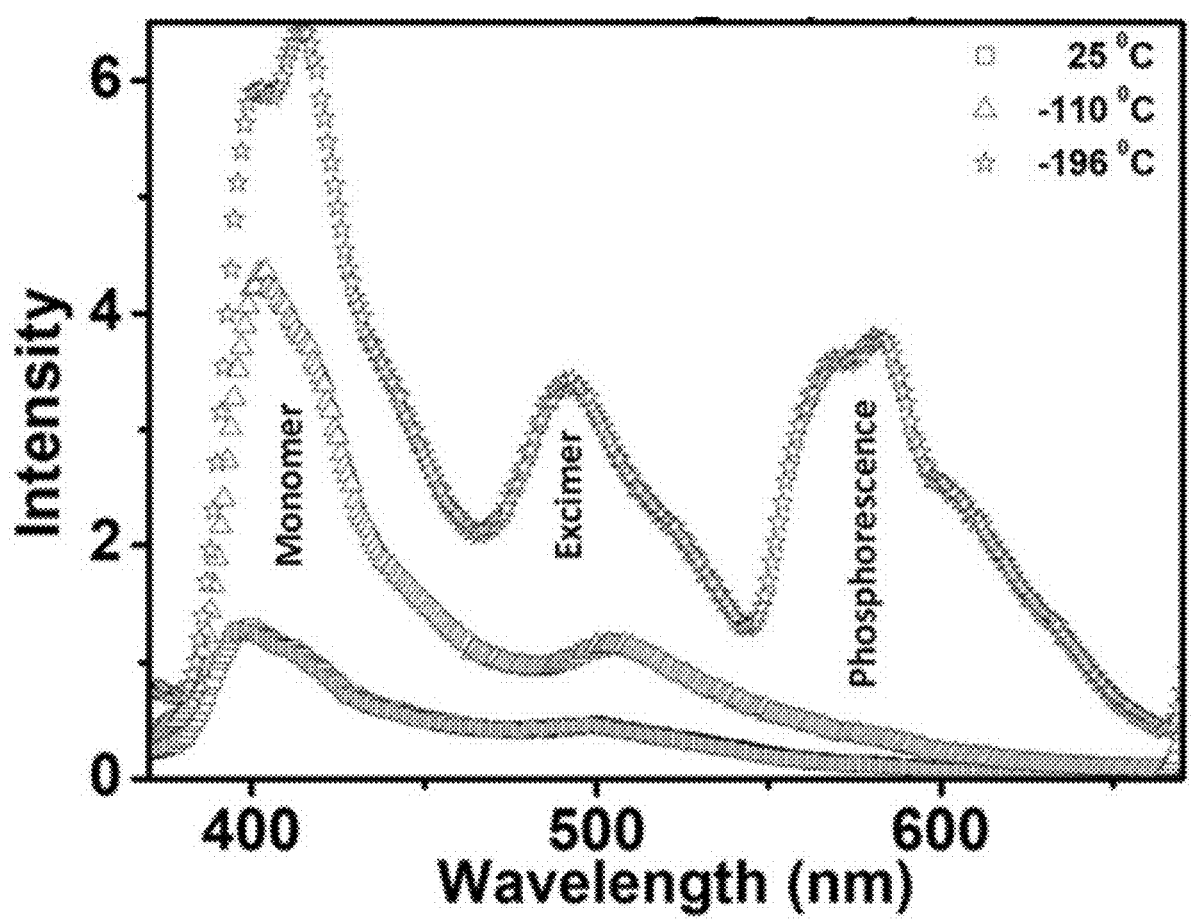

The thermometer comprises compounds of formulae 1a-1e and detects changes in temperature over a range of 30° C. to −196° C. by colour tenability from green to orange. Dipping compound of formula 1a in liquid nitrogen for a few seconds exhibited emission spectral changes as shown in FIG. 12A, a deep red to orange, green and blue colour is observed with time. The corresponding FIG. 12B indicates that these fluorescence colour changes are directly dependent on the temperature.

Figure 12C:
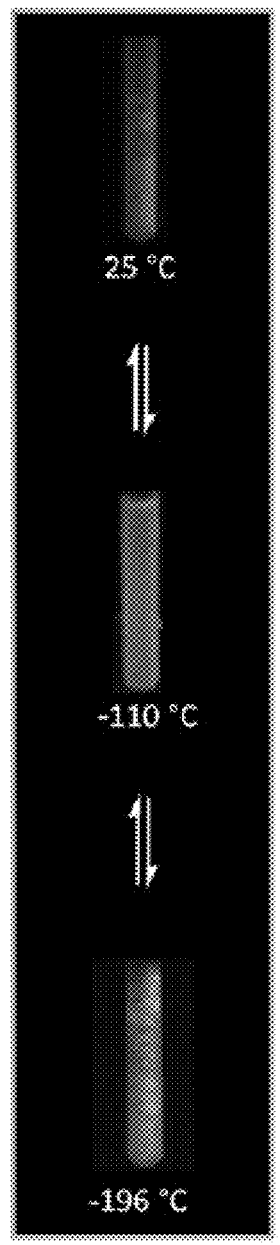
Figure 13A:
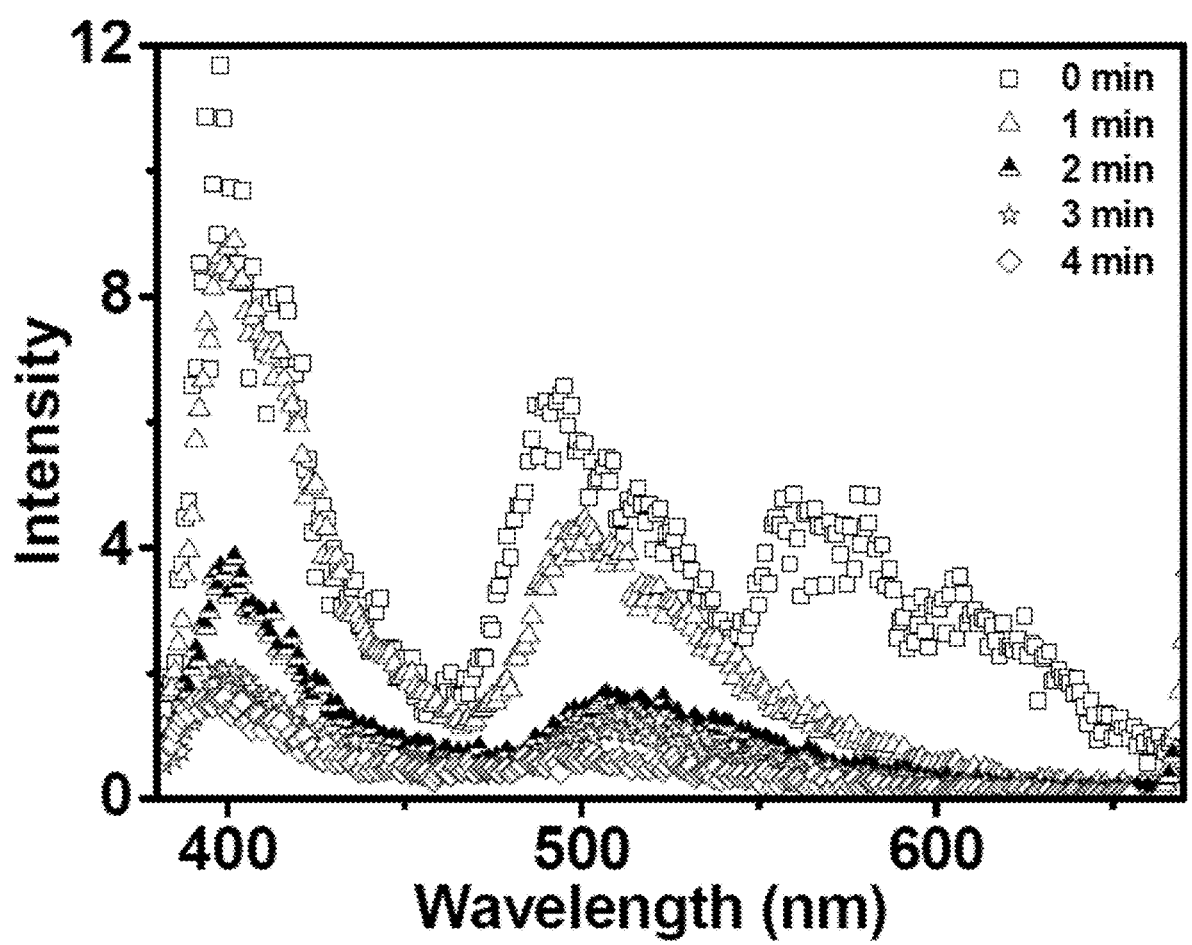
FIGS. 13A-D represent time dependent steady state emission spectra of (a) 1b, (b) 1c, (c) 1d and (d) 1e in MTHF solution from −196° C. to 25° C. in 4 min ($\lambda_{ex}$=342 nm, C=1×10$^{-2}$ M, l=1 cm).
Figure 13B:
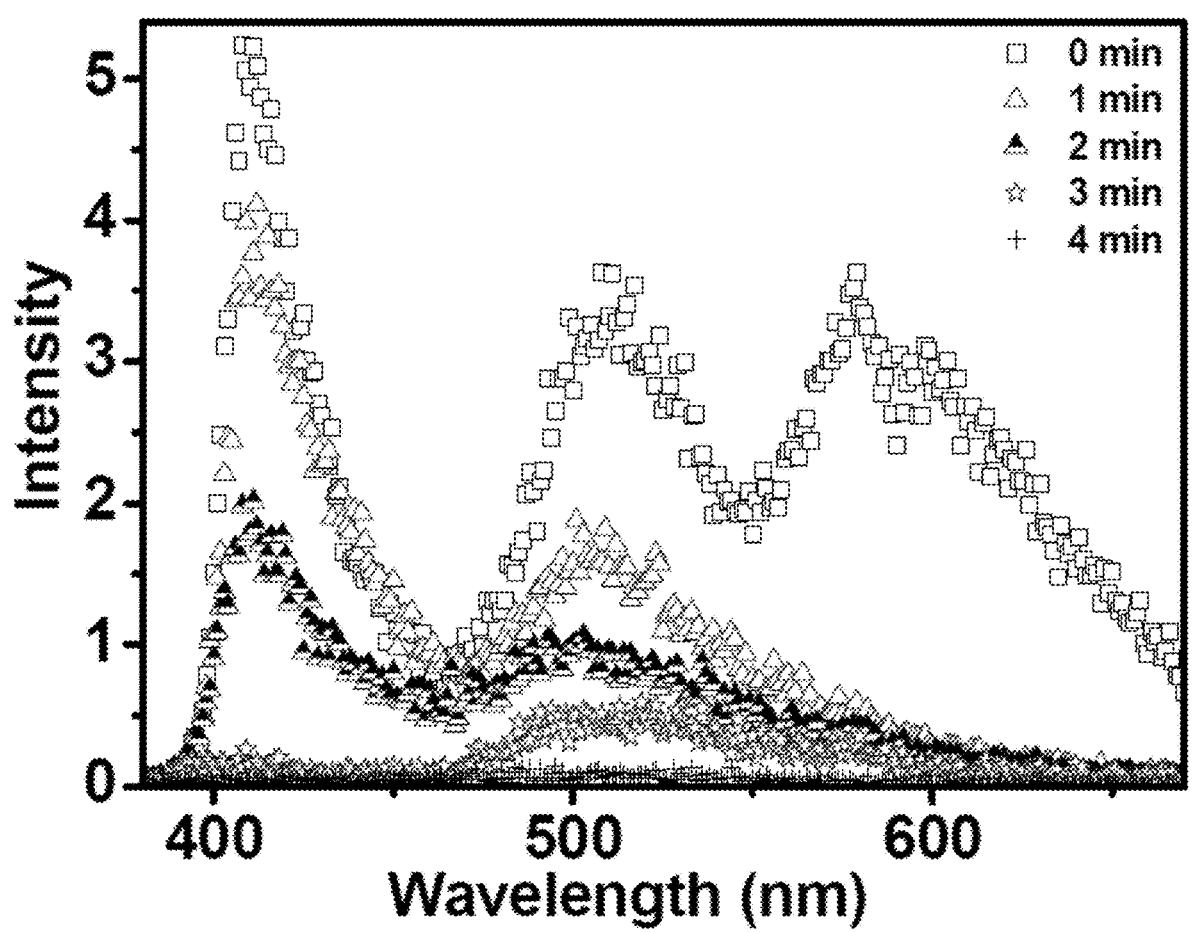
Figure 13C:
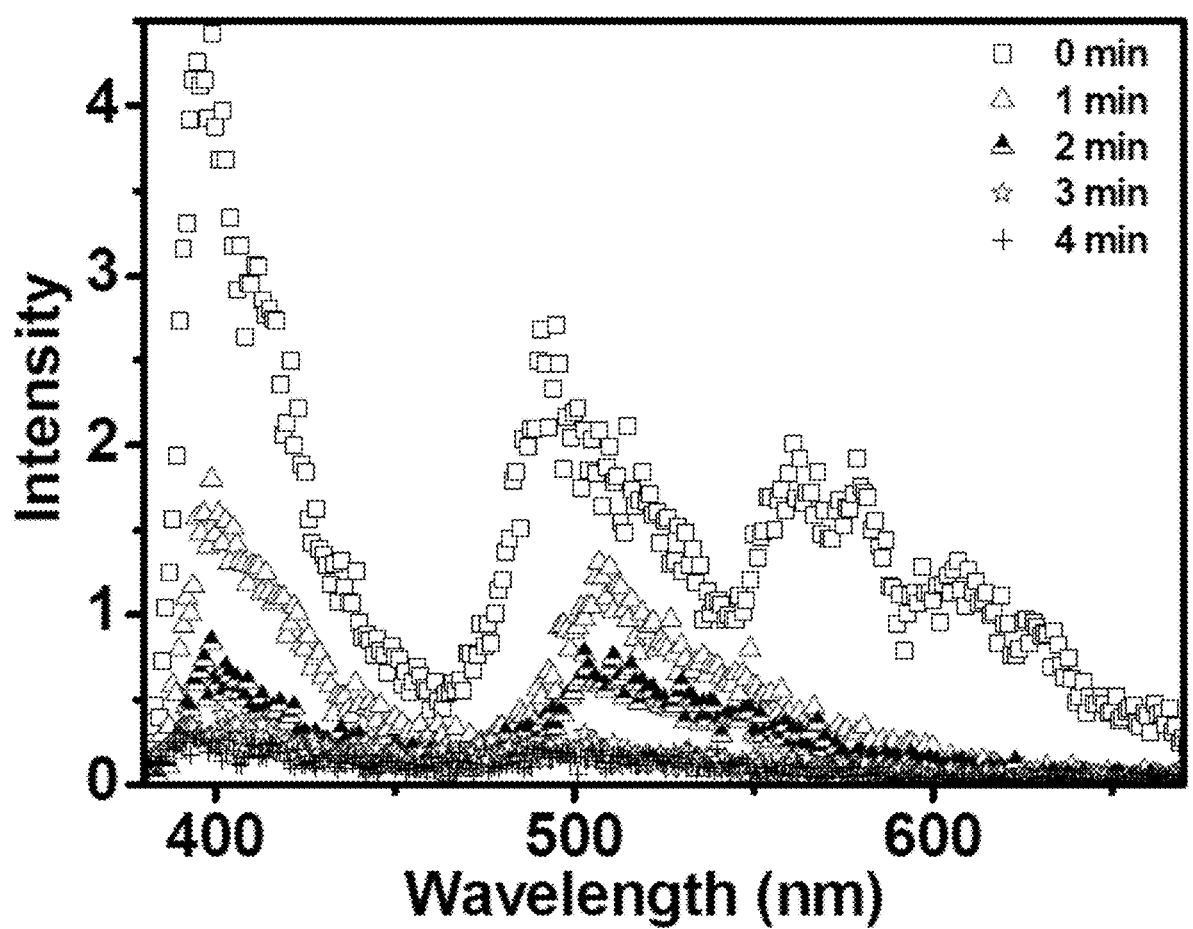
Figure 13D:
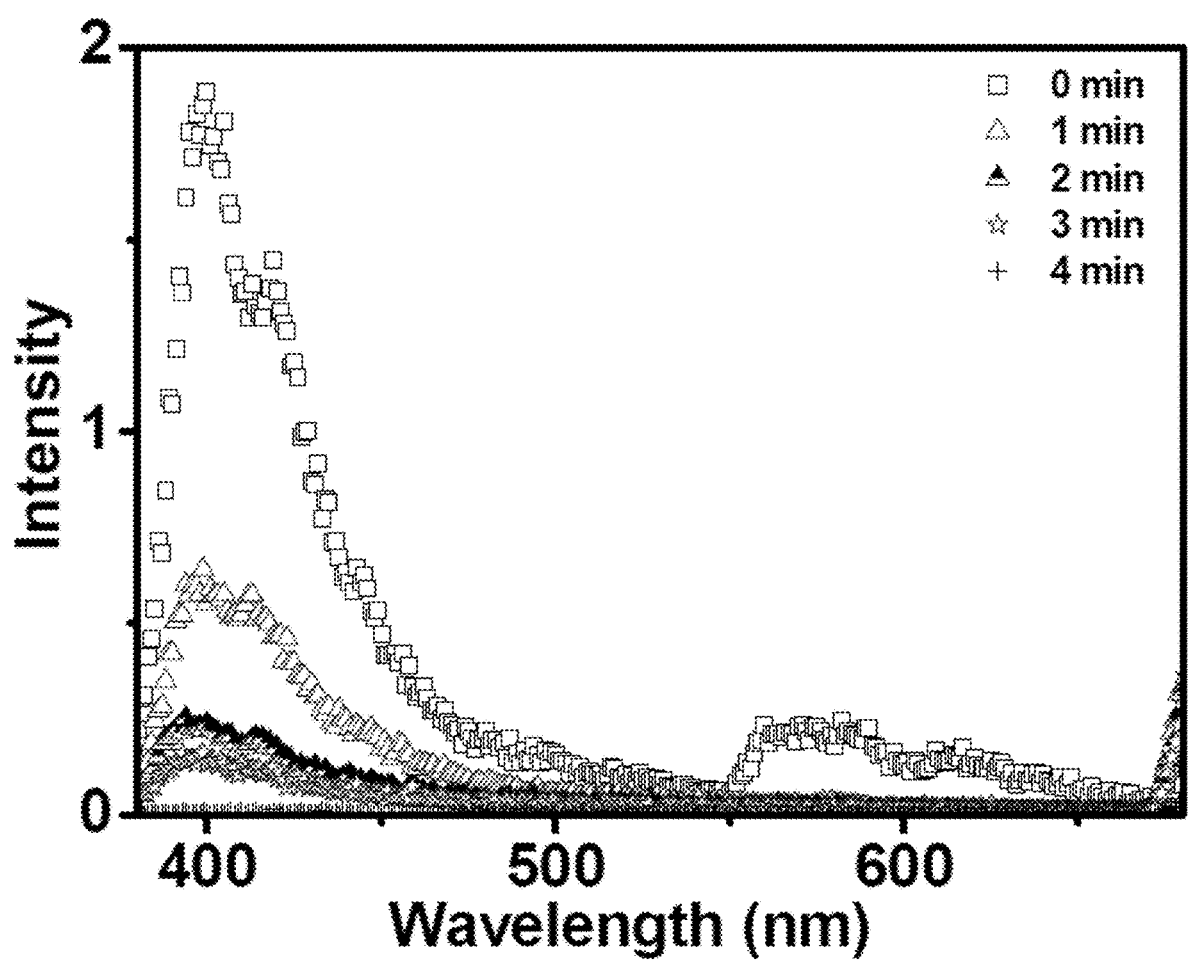
Figure 14A:
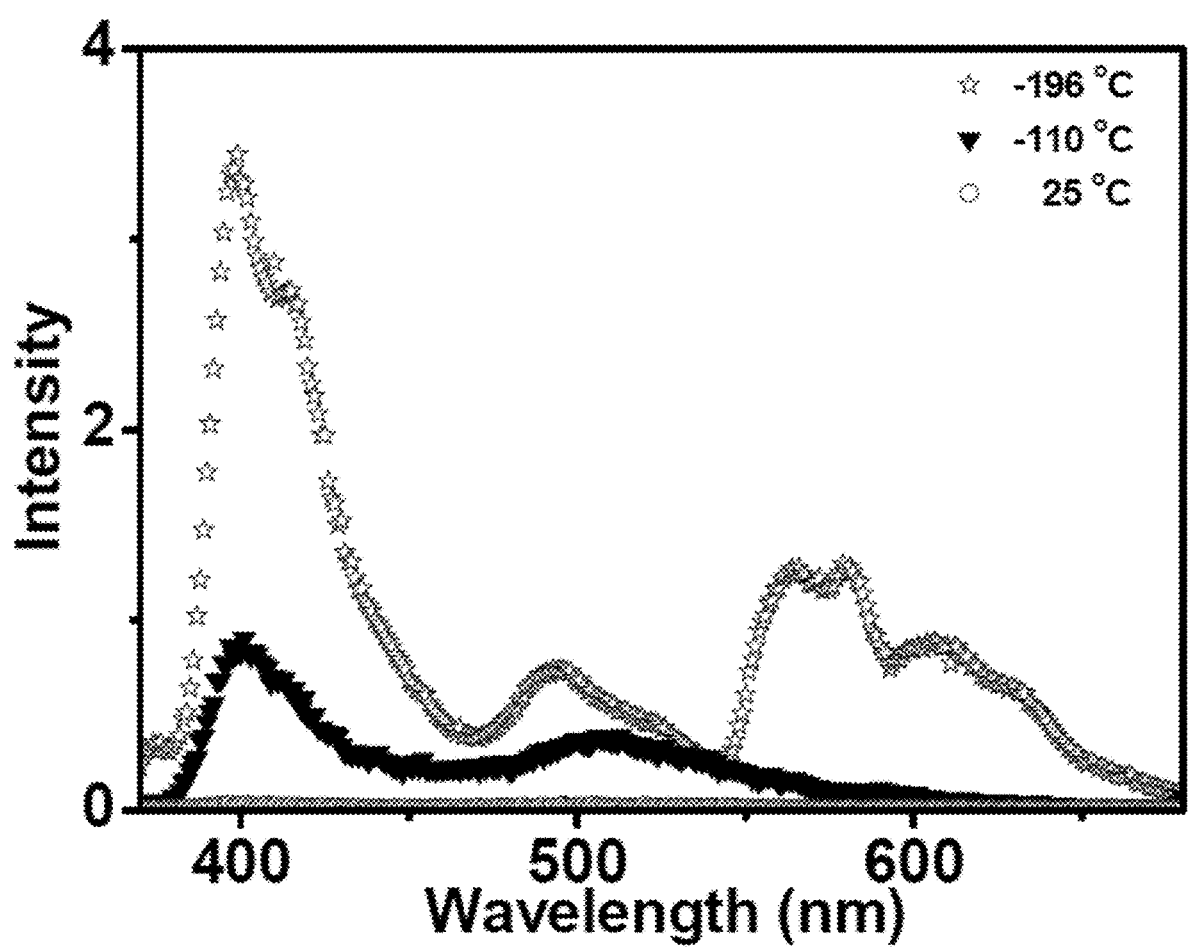
FIGS. 14A-D represent temperature dependent steady state emission spectra of (a) 1b, (b) 1c, (c) 1d and (d) 1e in MTHF solution at −196° C., −110° C. and 25° C. ($\lambda_{ex}$=342 nm, C=1×10$^{-5}$ M, l=1 cm).
Figure 14B:
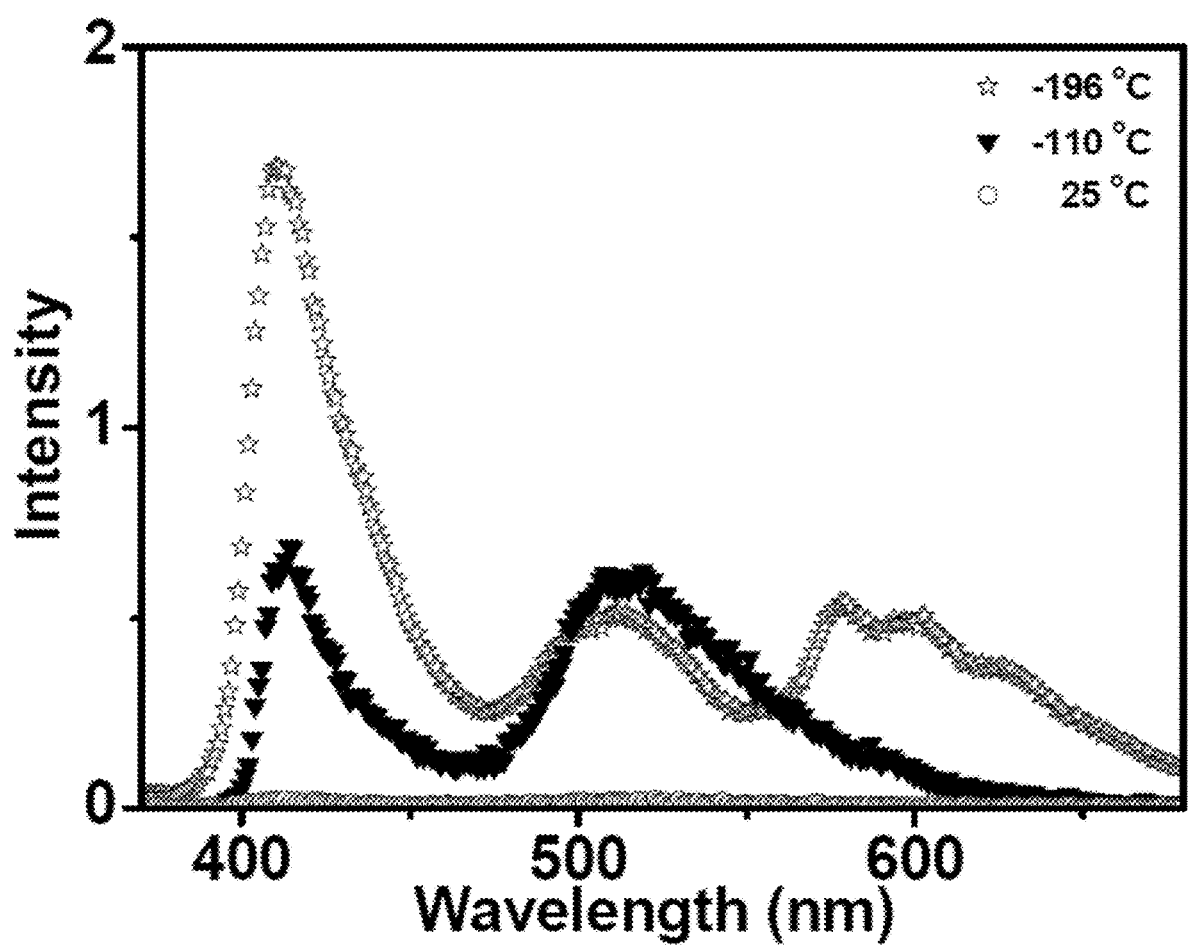
Figure 14C:
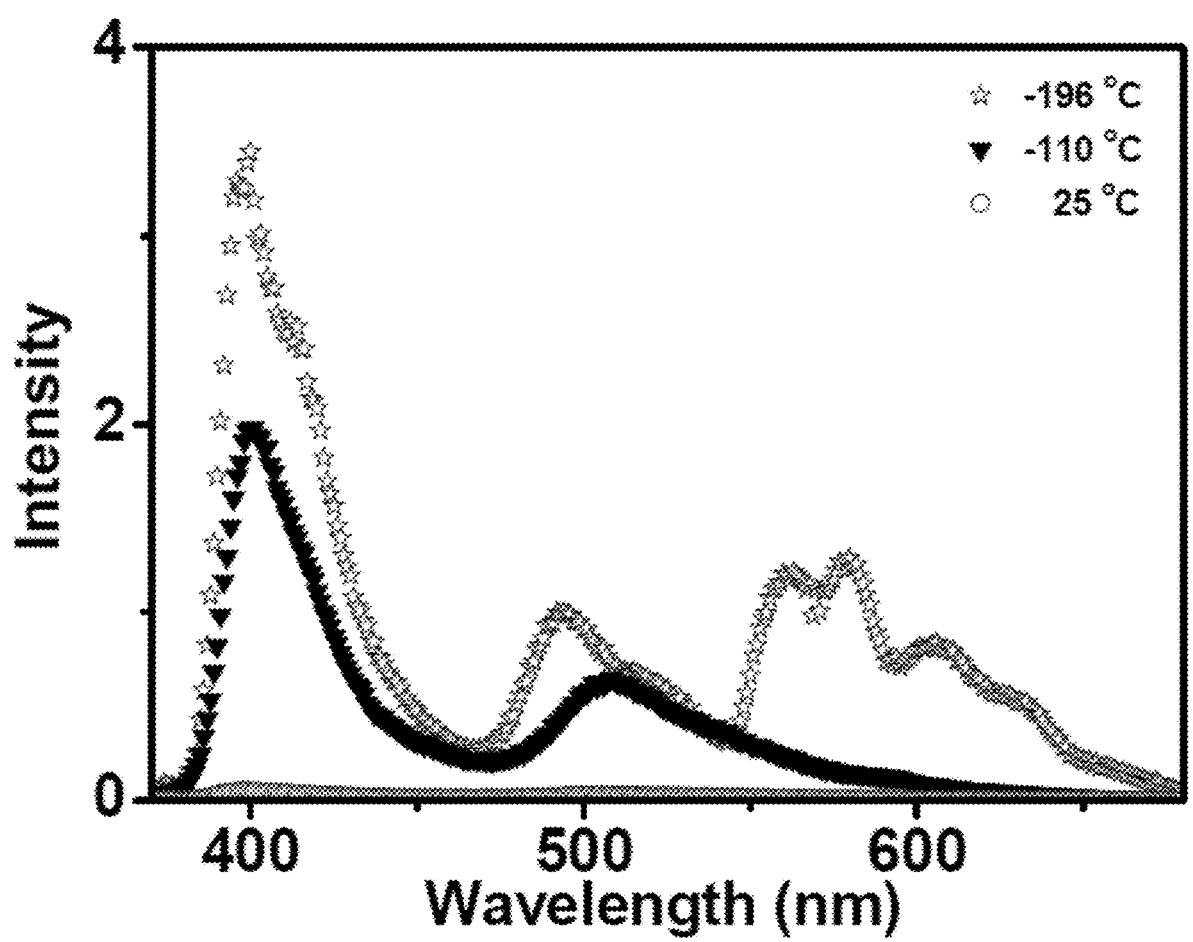
Figure 14D:
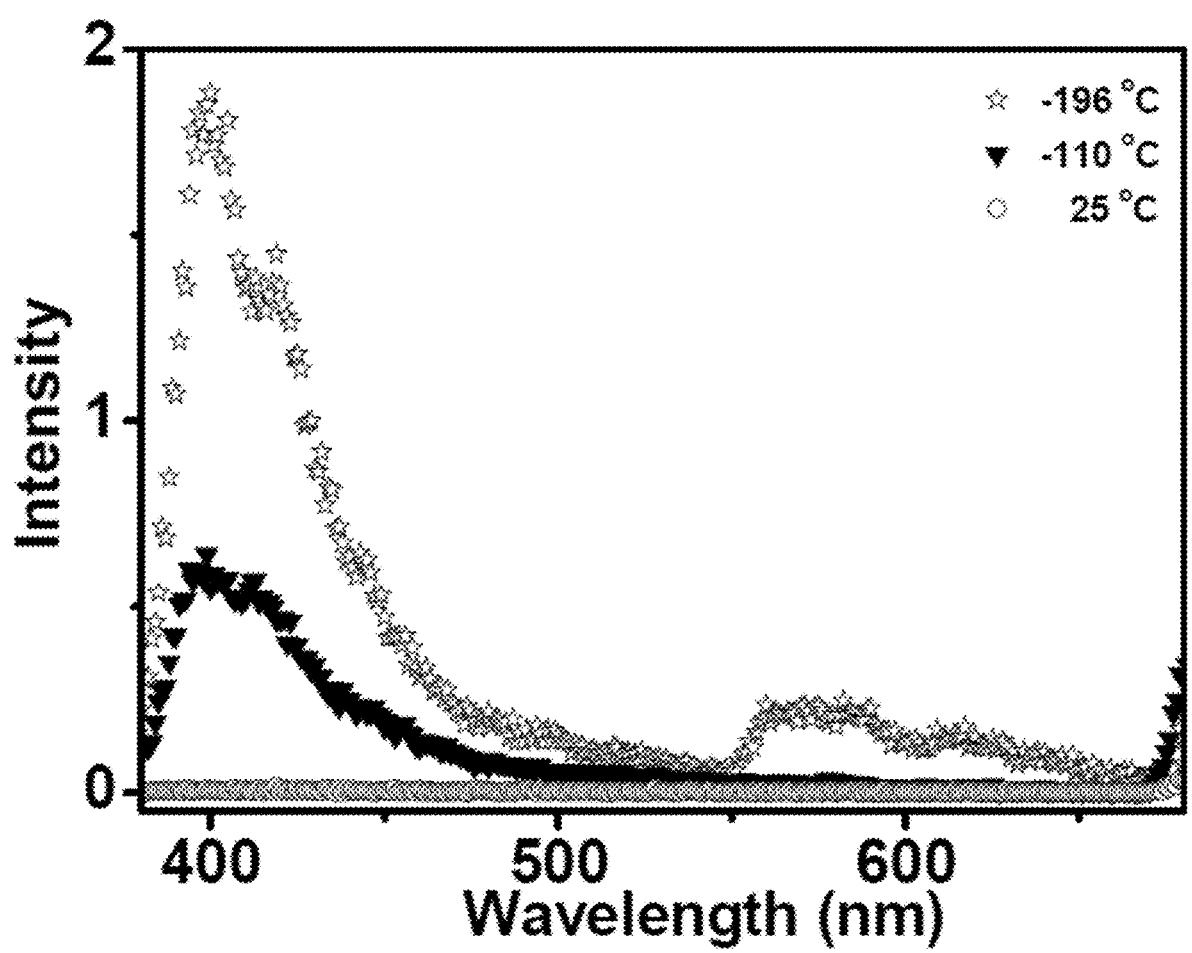

In an embodiment of the invention, the emission spectra of compound of formula 1a at various temperatures as shown in FIG. 12A is elicited. As the temperature is increased from 77K to 25° C., compound of formula 1a shows fluorescence variation from deep red to orange to yellow finally to green as shown in FIG. 12C. The emission spectrum of compound of formula 1a at 77K exhibits three major peaks due to phosphorescence (550-700 nm), excimer emission (450-550 nm) and monomer (380-450 nm) as shown in FIGS. 13A-D. The higher contribution of phosphorescence at 77K leads to the deep red colour. Phosphorescence intensity is gradually decreased with increase in temperature and hence excimer emission becomes dominant. The excimer green emission also finally disappears to show very faint blue emission from the monomer. The same trend of fluorescence variation with time and temperature in compounds of formulae 1b-d is shown in FIGS. 13A-D and 14A-D.

Figure 15A:
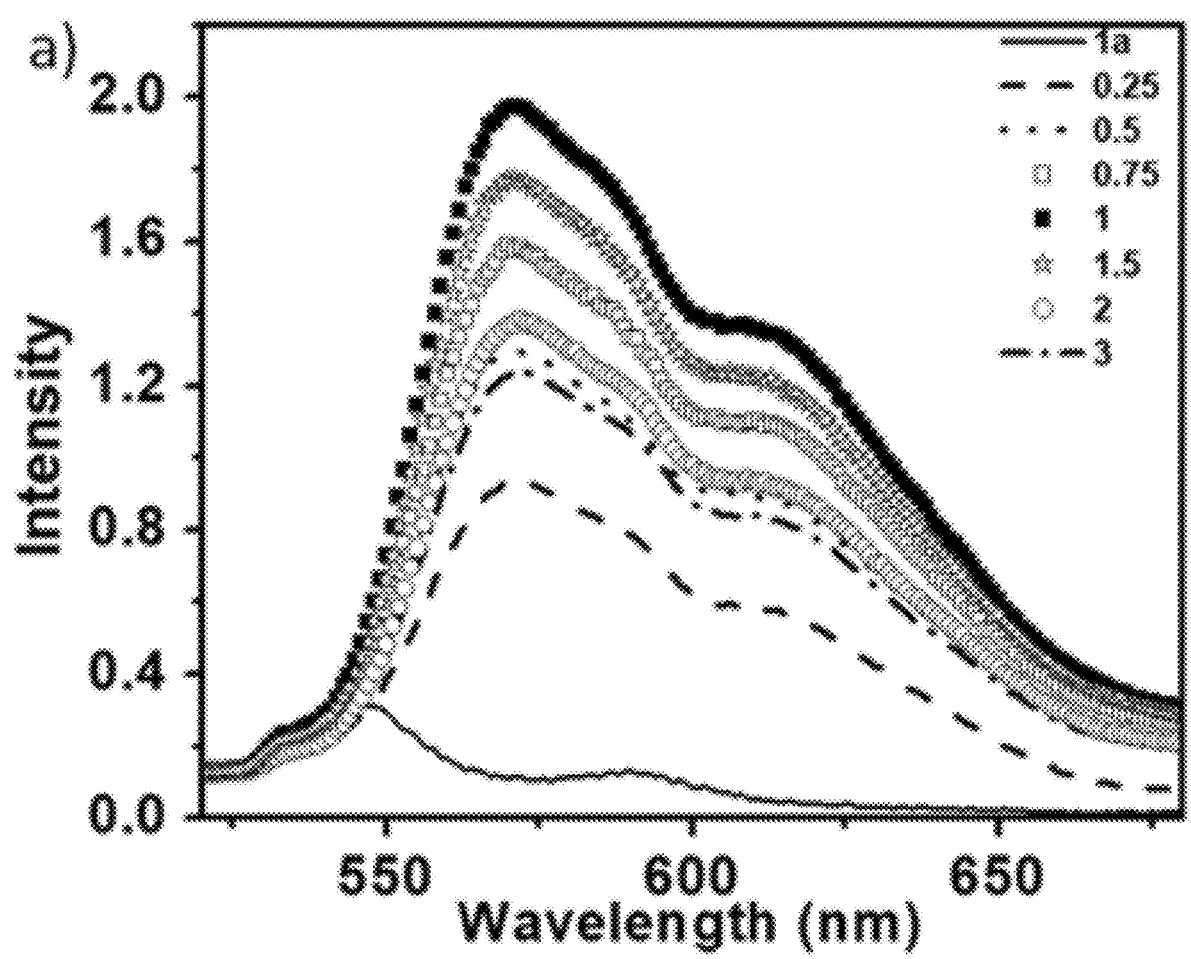
FIGS. 15A-D represent Phosphorescence spectral changes of 1e with increasing equivalents of (a) A2 and (b) A3 at RT in air with c) corresponding secondary plot for both 1a and 1e ($\lambda_{ex}$=345 nm). (d) Photograph of large area coating of 1e+A2 (1:1) RT liquid composite showing enhanced phosphorescence
Figure 15B:
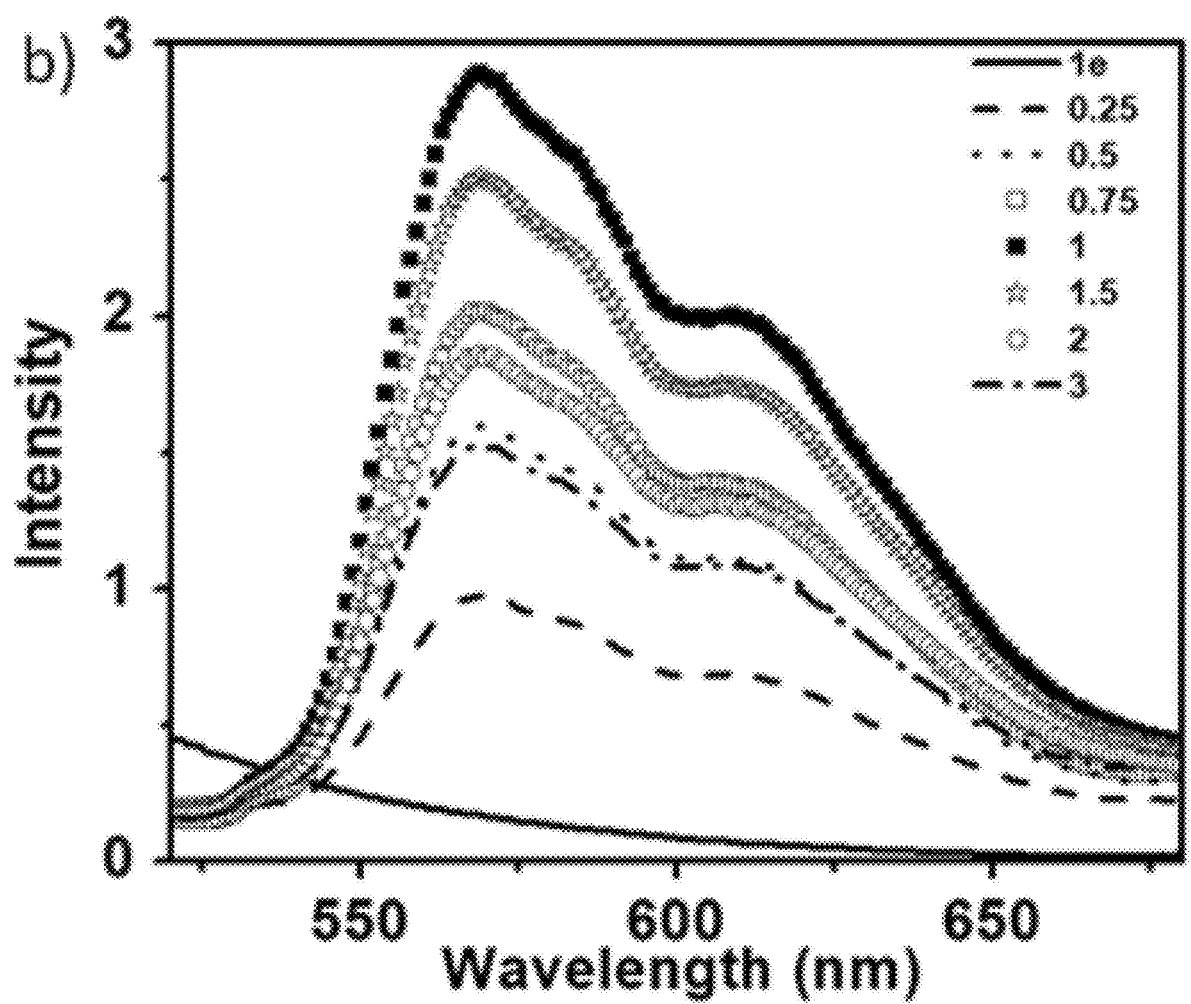
Figure 15C:
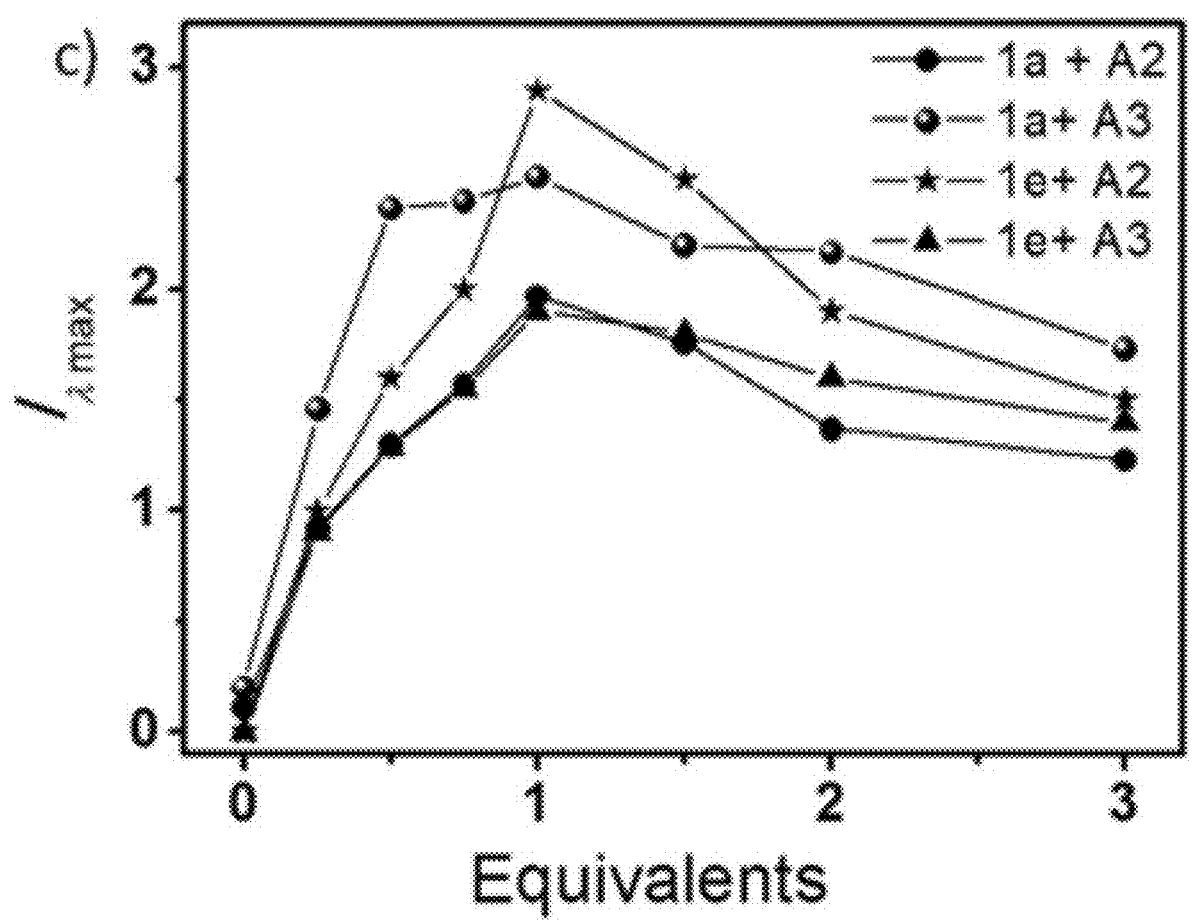
Figure 15D:
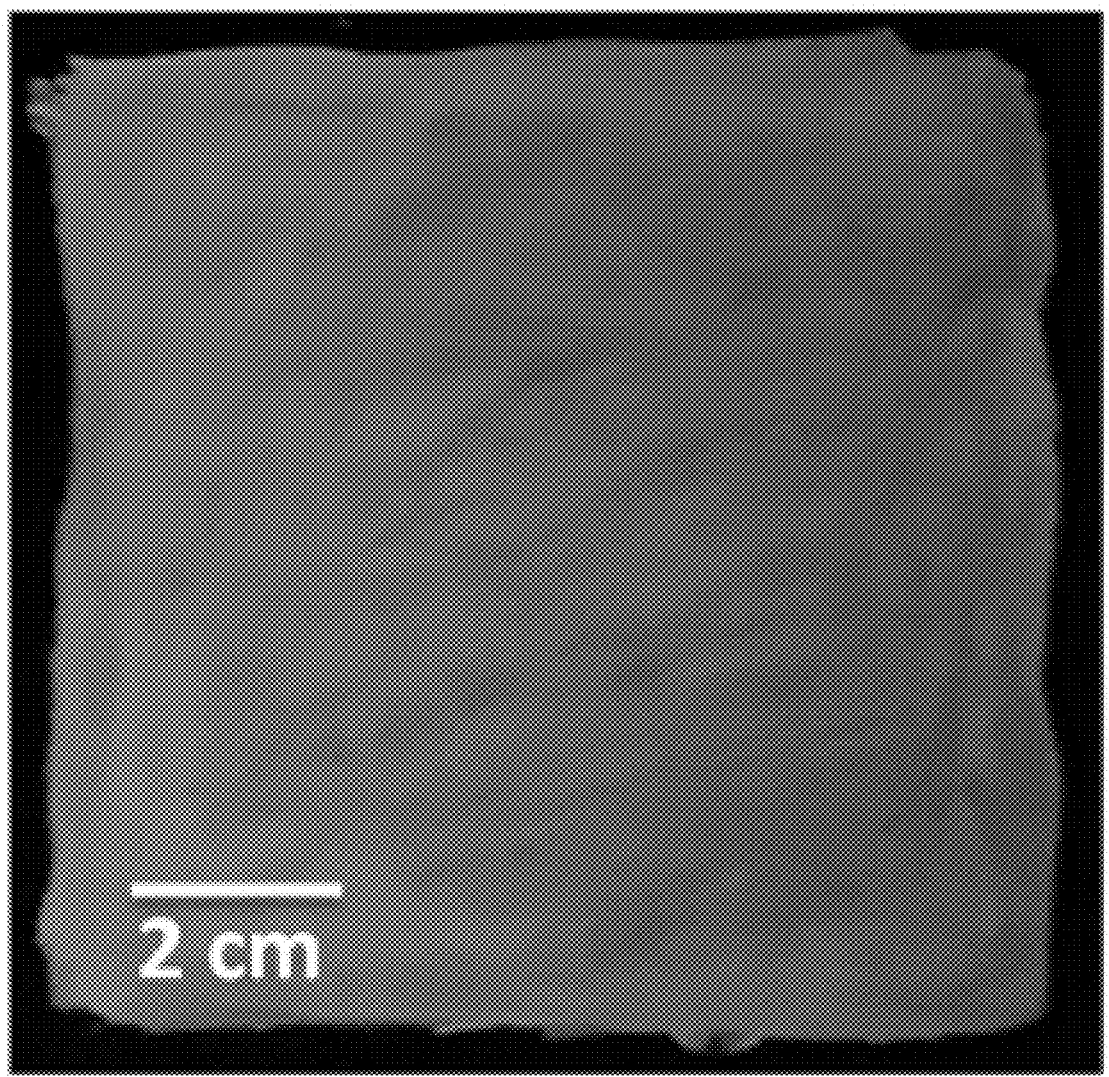
Figure 16A:
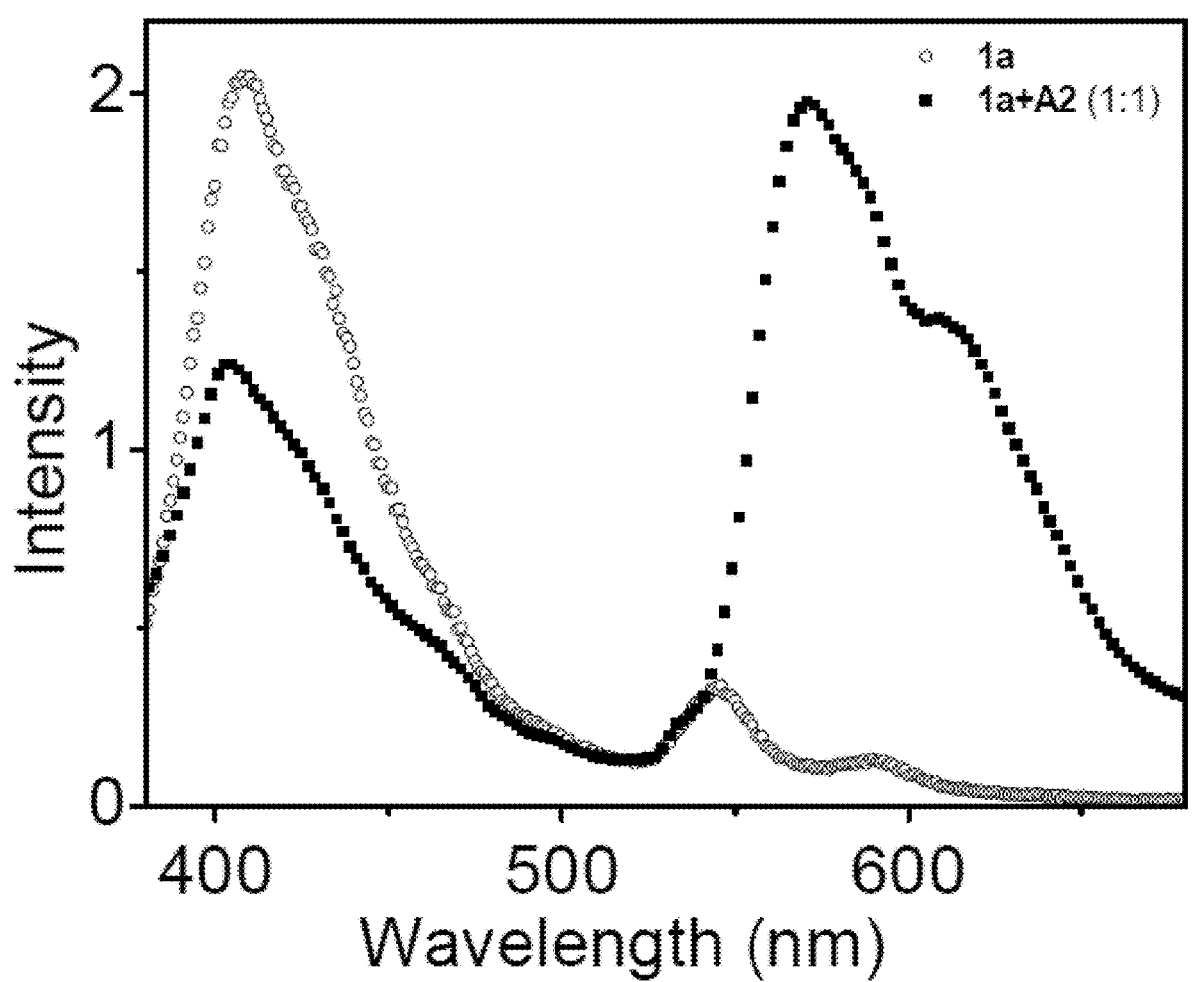
FIGS. 16A-B represent Luminescence spectral change of composites of a) 1a and 1e) with A2 (1:1) at 25° C.
Figure 16B:
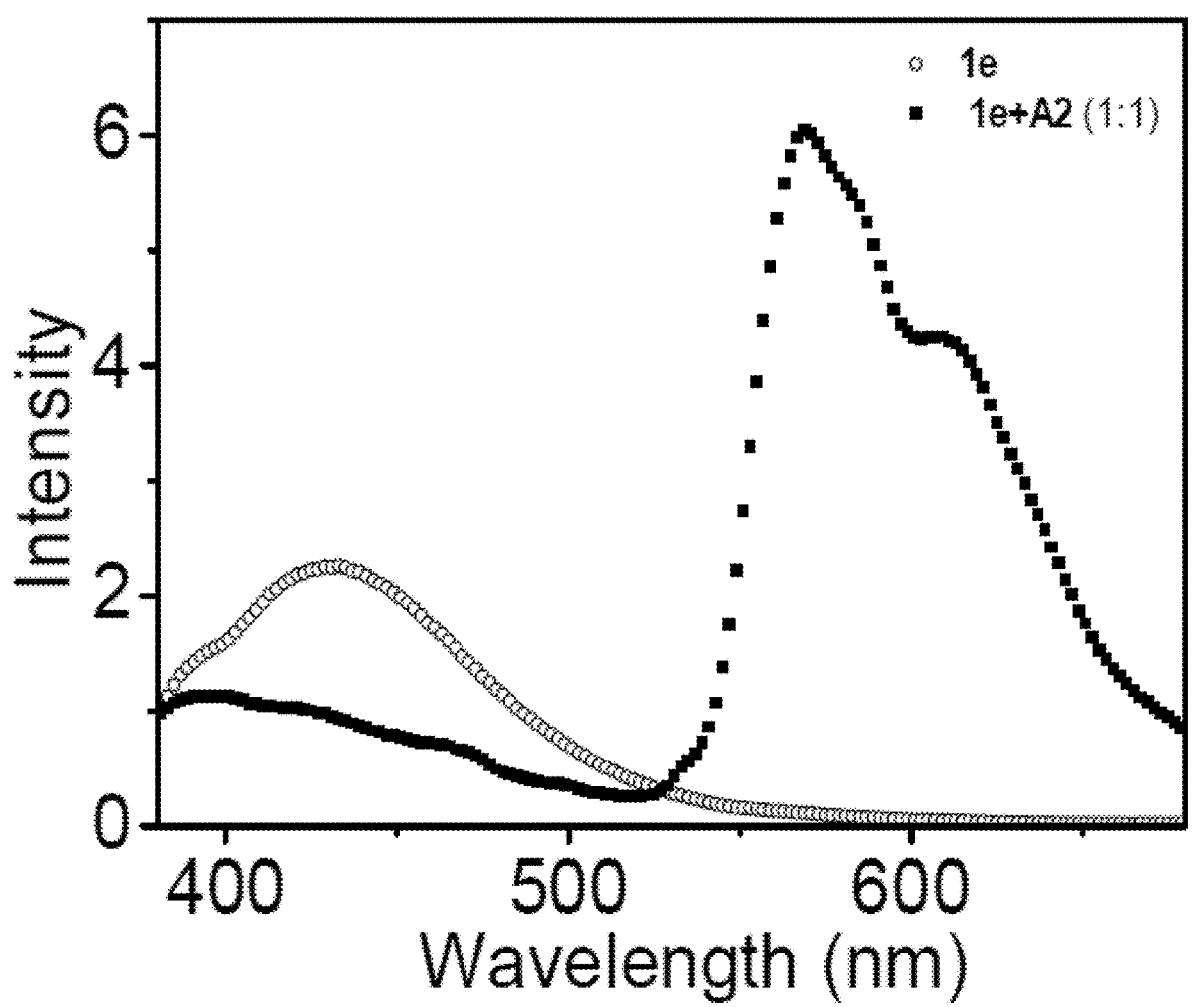
Figure 17A:
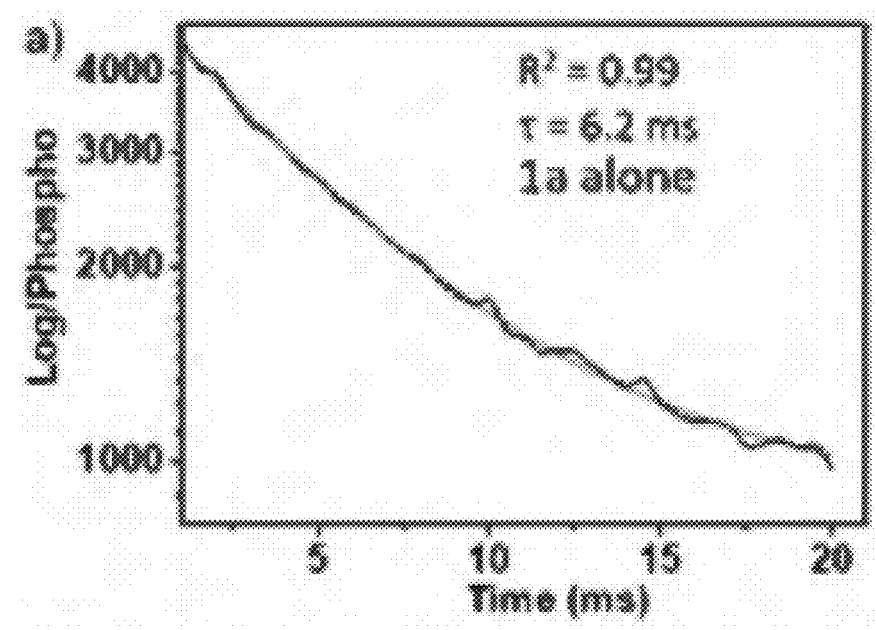
FIGS. 17A-F represent Phosphorescence lifetime decay profile of (a) 1a alone, (b) 1a+A2 (1:1), (c) 1a+A3 (1:1), (d) 1e alone, (e) 1e+A2 (1:1) and (f) 1e+A3 (1:1) in air at 30° C. ($\lambda_{ex}$=345 nm).
Figure 17B:
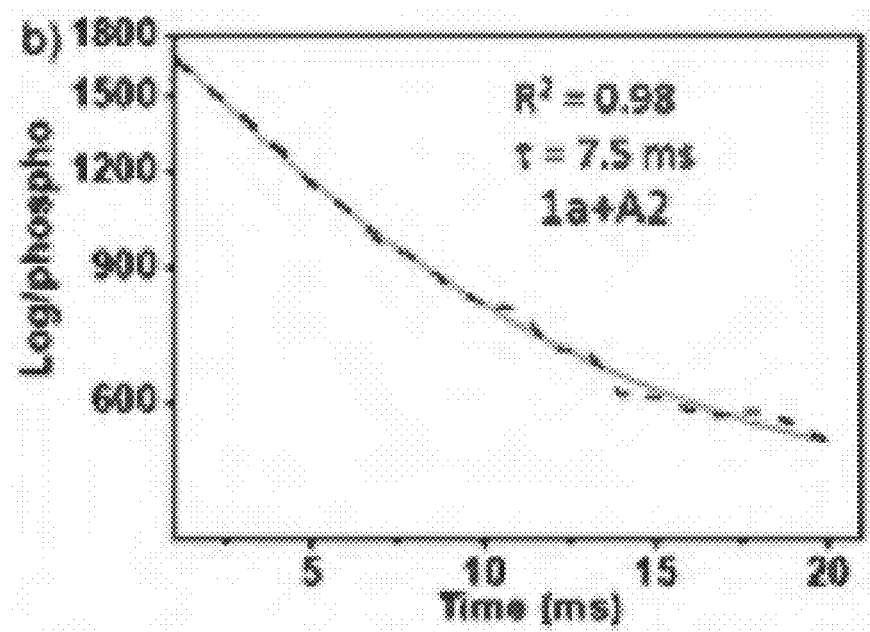
Figure 17C:
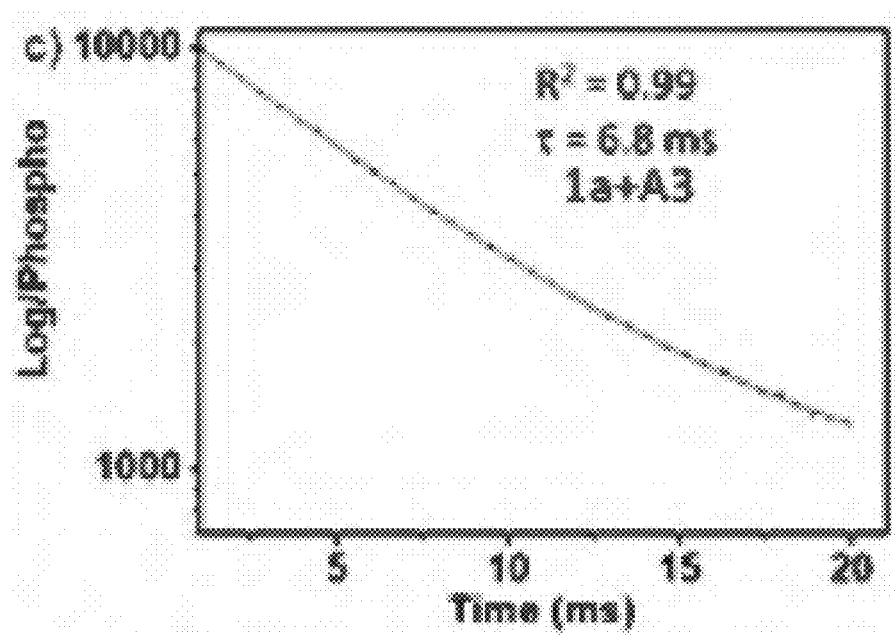
Figure 17D:
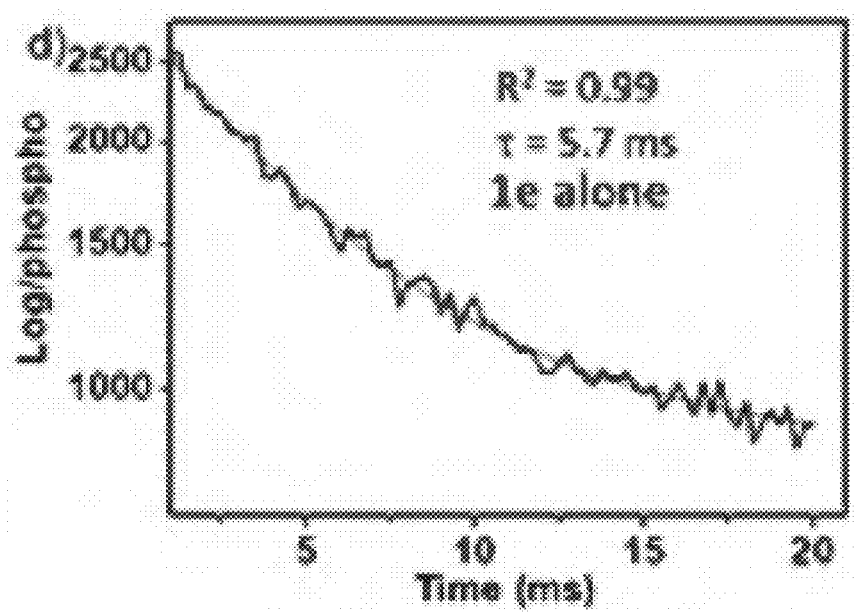
Figure 17E:
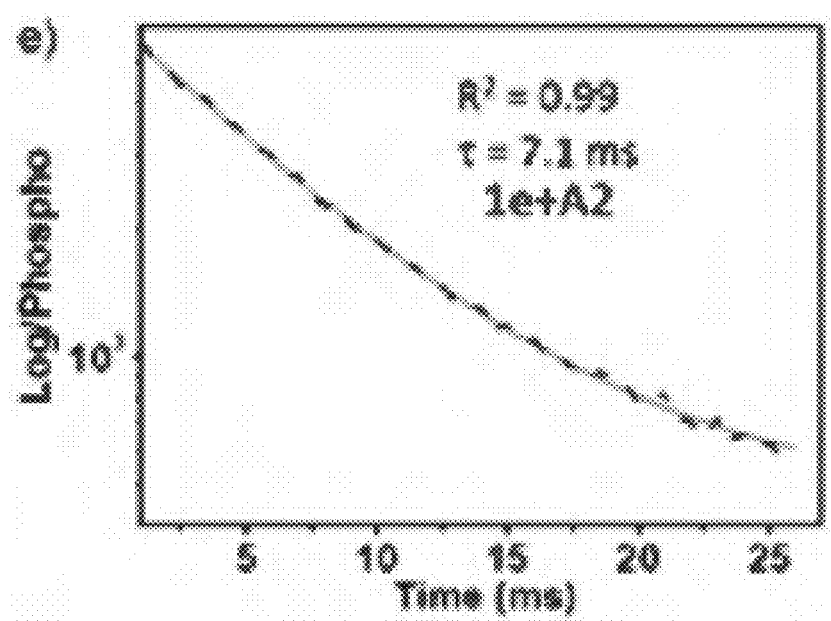
Figure 17F:
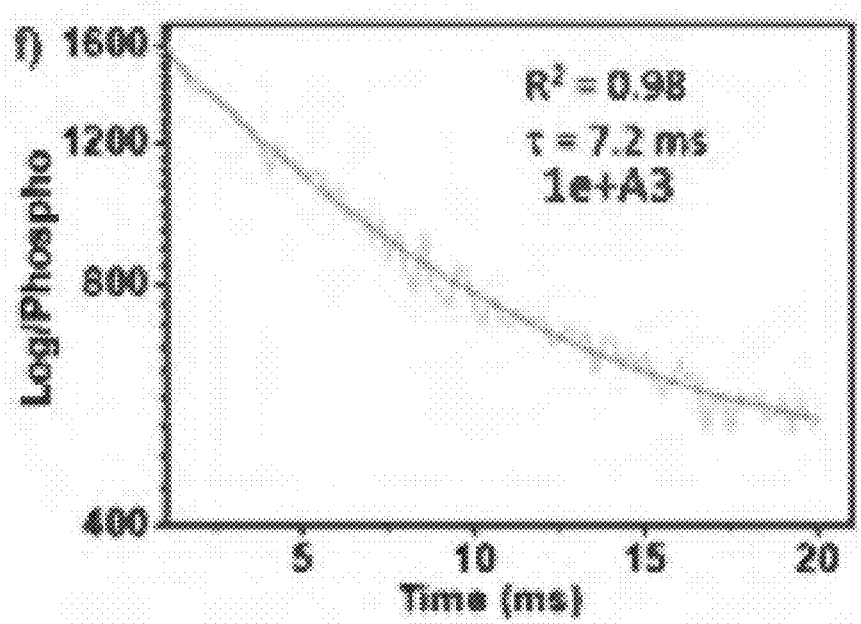

An ample way of improving phosphorescence by mixing with carbonyl compounds such as benzene-1,3,5-tricarbaldehyde (A3) and terephthalaldehyde (A2), which has intrinsic tendency to support phosphorescence via halogen bonding has been adopted for compounds of formulae 1a and 1e. A significant increment of phosphorescence intensity is observed for both compounds 1a and 1e upon mixing with increasing the equivalents of both the carbonyl compounds (A2, A3) at 25° C. in air as shown in FIGS. 15A and 15B. Among all the trials, 1:1 combination shows maximum phosphorescence enhancement as shown in FIG. 15C. Compound of formula 1e exhibits improved phosphorescence in combination with compound A2 (1:1), a liquid phosphor composite is developed by simple mixing of compound of formula 1e with compound A2 (1:1) and this combination realized a large area (10×10 cm) paintable composite with an improved phosphorescence at 25° C. as shown by FIG. 15D. The co-assembly formation suppresses monomer emission of both compounds of formulae 1a, 1e and improves phosphorescence as shown in FIGS. 16A-B. The advantage of carbonyl group of compounds A2 and A3 doping is reflected in enhancing both phosphorescence lifetime as shown in FIGS. 17A-B and quantum yield as summarized Table 3.

TABLE 3

Variation of absolute quantum yield of compounds 1a, 1e and 1:1 composites 1a + A3, 1a + A2, 1e + A3, 1e + A2.

| Sample | Absolute QY (%) |
|---|---|
| 1a | 0.1 |
| 1e | 0.1 |
| 1a + A3 (1:1) | 0.65 |
| 1a + A2 (1:1) | 3.96 |
| 1e + A3 (1:1) | 0.34 |
| 1e + A2 (1:1) | 2.01 |

The present invention is to provide formulation comprising new bromonapthalimide derivative compounds of formula (I) with fillers, additives, polymers, reinforcements, wherein the product or formulation displays solvent free liquid state phosphorescence. A paintable phosphorescent liquid composite with enhanced luminescent quantum yield and lifetime is provided.

In particularly preferred embodiment, the present invention provides a formulation comprising a compound, 6-bromo-2-(tricosan-12-yl)-1H-benzo[de]isoquinoline-1,3 (2H)-dione of formula (1e) in the range of 0.1-99% with fillers, additives, polymers, reinforcements in the range of 1-99.9%, wherein the product or formulation displays solvent free liquid state phosphorescence. Liquid feature of compound of formula 1e at 25° C. enables to deliver a paintable phosphorescent composite at 25° C. in neat form and this provides a potential alternate for the tedious and expensive processing methods of crystalline phosphors at 25° C.

Preparation of Thin Film

Quartz plate was dipped in 1 mM of MTHF solution of 1a and 1e and allowed to completely dry for 5 min. The thin film formed on one side of the quartz plate was carefully removed by wiping with solvent.

Preparation of Phosphorescent Composites

The finely powdered carbonyl guest molecules are mixed with the liquid phosphor 1e in a mortar by mechanical grinding for 15 min to get a uniform composite. If the solid dopants are not miscible with the liquid matrix, 1-2 mL of dichloromethane was added to make a homogeneous mixture. The added dichloromethane was evaporated before phosphorescence measurements by heating the composite to 80° C. and the homogeneity of the composite is confirmed by the physical appearance and DSC measurements. In the case of 1a, thin films of composites are prepared by dropcasting/spin coating of dichloromethane solution of 1a and dopants.

Phosphorescence Experiments

All phosphorescence experiments have done in air by keeping the same experimental parameters. The window of maximum delay after flash for phosphorescence measurements was kept as 3 ms for −196° C. and 0.5 ms for 25° C.

Temperature Dependent Thermometer

Experimental Procedure 1a and 1e are dissolve in 1 ml MTHF (1 mM) and filled in quartz NMR tube, this filled NMR tube is dipped in each temperature bath which is prepared already (−196° C., −112° C. and 25° C.).

−196° C. temperature bath: NMR tube is dipped in liquid nitrogen alone and emission is red for both 1a and 1e.

−112° C. temperature bath: NMR tube is dipped in bath which is prepared by mixing liquid nitrogen and ethanol and emission is green for both 1a and blue for 1e.

Explanation of Temperature Dependent Thermometer

Figure 18A:
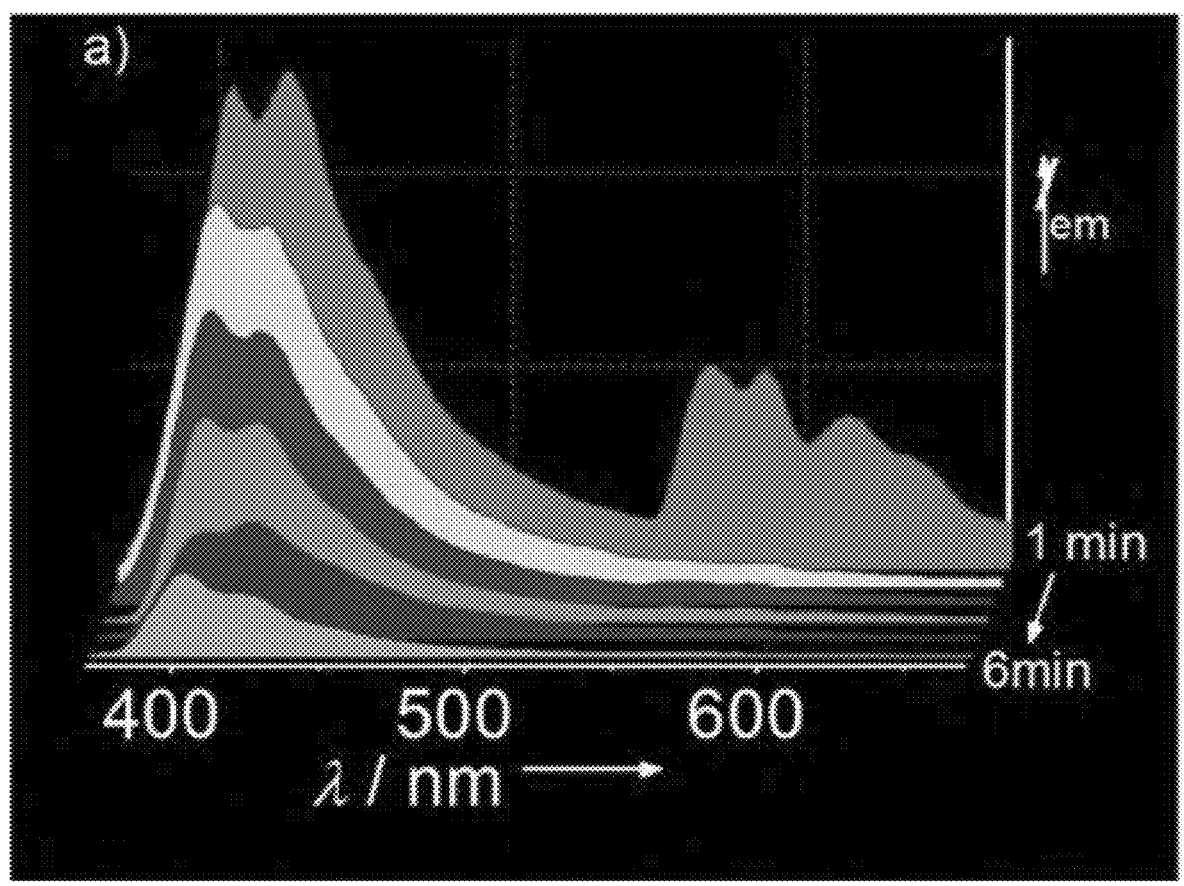
FIGS. 18A-B represent time temperature dependent tunable emission spectral changes of compound of formula 1e after dipping the solution in liquid $N_2$ (a) Temperature dependent tunable emission spectral changes of compound of formula 1e (b) with corresponding photographs showing reversible tunable emission colours; blue at 25° C., green at −110° C. and red at −196° C. (inset).
Figure 18B:
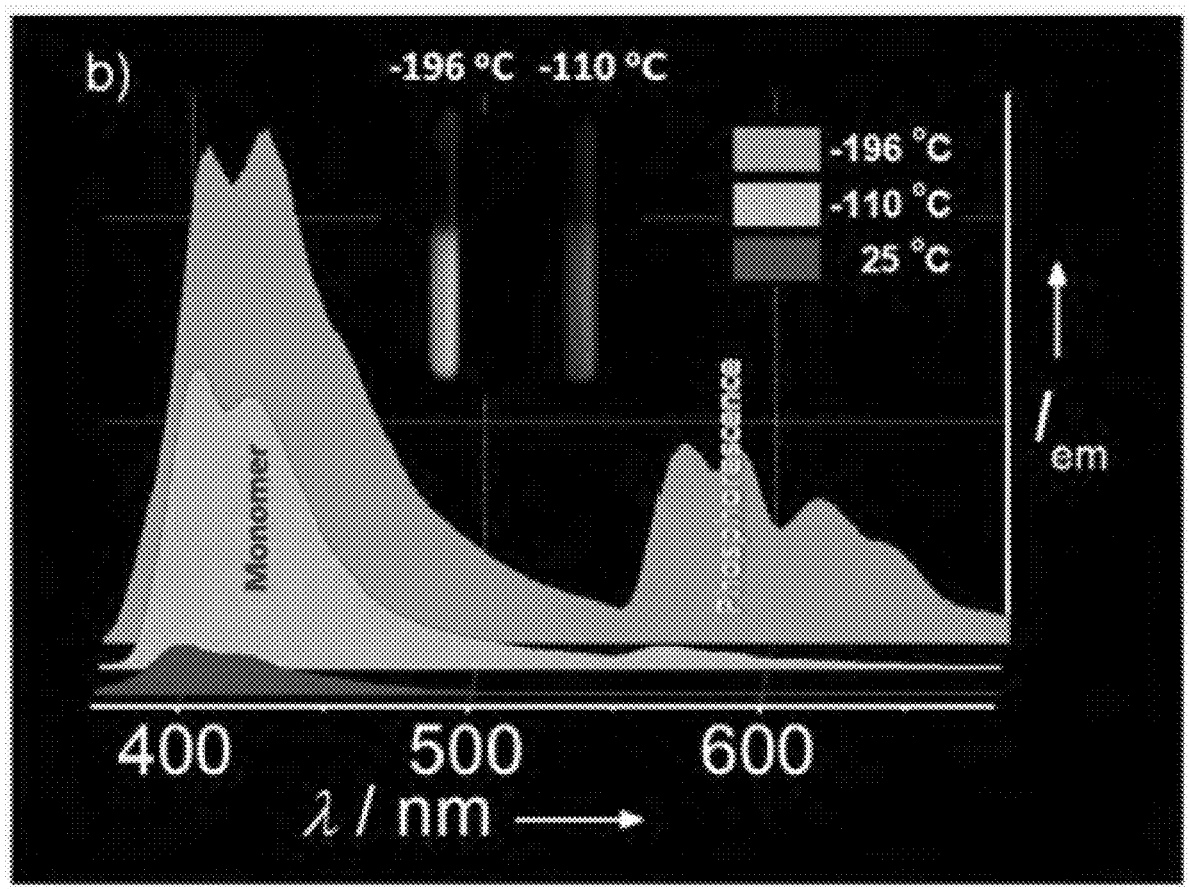

Upon monitoring the luminescence of 1a in MTHF solution after dipping in liquid $N_2$ for 10 seconds, a deep red to green and further to blue luminescence colour change is observed with time. In order to confirm this, the luminescence spectra of 1a was checked at various temperatures and it exhibits three major peaks at −196° C. due to phosphorescence (550-700 nm), excimer (450-550 nm) and monomer (380-450 nm) emissions. The major contribution of phosphorescence at −196° C. leads to red colour. Phosphorescence intensity is gradually decreased with increase in temperature and hence excimer emission becomes dominant at around −110° C. The green excimer emission also finally disappears to show blue emission from the monomer with reduced quantum yield at 25° C. The corresponding photographs (FIGS. 12A-B) indicate the possible thermoreversible tunable luminescence and can be explored for a luminescence based thermometer to monitor temperature variation from −196° C. to 25° C. However, in the case of 1e (FIGS. 18A-B), the steric bulkiness of the branched, long alkyl chains prevents to form excimer even at very low temperature and hereby it justifies the molecular design. Temperature variation from −196° C. to −80° C. resulted in a direct red to blue luminescence colour change for 1e. Hence luminescence colour tunability similar to that of 1a is not achieved by 1e.

EXAMPLES

Following examples are given by way of illustration therefore should not be construed to limit the scope of the invention.

The compounds 1a-d are synthesized by reported methods, refer (a) H. Mu, R. Gong, Q. Ma, Y. Sun and E. Fu, *Tet. Let.*, 2007, 48, 5525; (b) W. Wu, W. Wu, S. Ji, H. Guo, P. Song, K. Han, L. Chi, J. Shaoa and J. Zhao, *J. Mater. Chem.*, 2010, 20, 9775.

Example 1: General Procedure for Synthesis of Compounds of Formulae 1a-1d

A mixture of 1, alkylamine and ethanol was taken in an RB flask and heated at 87° C. under argon atmosphere for 12 hr. After cooling to 30° C., the solid that precipitated was filtered and washed with ethanol. Solvent was removed by vacuum to get pure compound.

Example 2: Synthesis of 6-bromo-2-butyl-1H-benzo[de]isoquinoline-1,3(2H)-dione (1a)

1 (500 mg, 1.80 mmol), butylamine (197.98 mg, 2.71 mmol), and distilled ethanol (20 mL). Pale yellow solid, Yield: 81%.

$^1$H NMR (400 MHz, CDCl$_3$), δ (TMS, ppm): 8.65 (d, J=7.32, 1H), 8.56 (d, J=8.54, 1H), 8.41 (d, J=7.93, 1H), 8.06 (d, J=7.93, 1H), 7.85 (t, J=7.32, 1H), 4.18 (t, J=7.32, 2H), 1.72 (m, 2H), 1.46 (m, 2H), 0.99 (t, J=7.32, 3H); $^{13}$C NMR (100 MHz, CDCl$_3$), δ (TMS, ppm): 163.63, 132.20, 132.00, 131.19, 131.08, 130.62, 130.17, 129.00, 128.06, 123.16, 122.29, 40.37, 30.15, 20.36, 13.82; FTIR ($v_{max}$ in cm$^{-1}$): 3022.83, 2959.37, 1701.24, 1659.76, 1584.65, 1515.91, 1352.77, 1217.18, 1076.26, 1031.71, 933.38, 860.22, 764.22, 669.90; MALDI-TOF: Calculated: 331.0208, found: 331.9519.

Example 3: Synthesis of 6-bromo-2-octyl-1H-benzo[de]isoquinoline-1, 3(2H)-dione (1b)

1 (500 mg, 1.80 mmol), octylamine (197.98 mg, 2.71 mmol) and distilled ethanol (20 mL). Pale yellow solid, Yield: 74%

$^1$H NMR (400 MHz, CDCl$_3$), δ (TMS, ppm): 8.66 (d, J=7.25, 1H), 8.56 (d, J=8.39, 1H), 8.41 (d, J=8.01, 1H), 8.05 (d, J=8.01, 1H), 7.85 (t, J=7.63, 1H), 4.17 (t, J=7.63, 2H), 1.73 (m, 2H), 1.43 (s, 10H), 0.88 (t, J=6.48, 3H); $^{13}$C NMR (125 MHz, CDCl$_3$), δ (TMS, ppm): 163.59, 133.19, 131.99, 131.18, 131.08, 130.63, 130.15, 129.01, 128.06, 123.18, 122.33, 40.63, 31.80, 29.32, 29.20, 28.08, 27.12, 22.62, 14.07; FTIR ($v_{max}$ in cm$^{-1}$): 3104.33, 3069.14, 3031.18, 2921.77, 2857.92, 1979.21, 1928.18, 1699.38, 1655.94, 1582.77, 1504.58, 1451.75, 1354.74, 1229.80, 1176.29, 1094.91, 1050.24, 938.83, 861.58, 763.93, 664.75; MALDI-TOF: Calculated: 387.0834, found: 387.9383.

Example 4: Synthesis of 6-bromo-2-dodecyl-1H-benzo[de]isoquinoline-1,3(2H)-dione (1c)

1 (500 mg, 1.80 mmol), dodecylamine (501.73 mg, 2.71 mmol) and distilled ethanol (20 mL). Pale yellow solid, Yield: 76%.

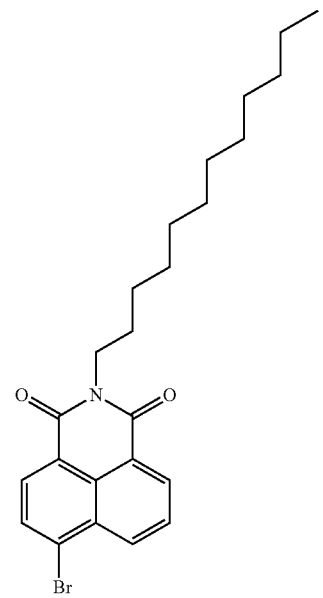 [SMILES: CCCCCCCCCCCCN1C(=O)c2cccc3c(Br)ccc(c23)C1=O]

$^1$H NMR (400 MHz, CDCl$_3$), δ (TMS, ppm): 8.65 (d, J=7.33, 1H), 8.56 (d, J=7.58, 1H), 8.40 (d, J=7.96, 1H), 8.03 (d, J=7.96, 1H), 7.86 (t, J=7.45, 1H), 4.17 (t, J=7.45, 2H), 1.73 (m, 2H), 1.26 (m, 18H), 0.88 (t, J=5.94, 3H); $^{13}$C NMR (100 MHz, CDCl$_3$), δ (TMS, ppm): 163.61, 133.19, 132, 131.19, 131.08, 130.65, 130.16, 129.03, 128.07, 123.20, 122.34, 40.64, 31.91, 29.62, 29.34, 28.09, 27.12, 22.68, 14.11; FTIR ($v_{max}$ in cm$^{-1}$): 3022.80, 2927.60, 2857.59, 1701.02, 1659.57, 1584.43, 1514.48, 1451.66, 1352.55, 1217.14, 1035.50, 927.55, 857.66, 763.59, 669.71; MALDI-TOF: Calculated: 443.4130, found: 444.1546.

Example 5: Synthesis of 6-bromo-2-(2-ethylhexyl)-H-benzo[de]isoquinoline-1,3(2H)-dione (1d)

1 (400 mg, 1.44 mmol), ethylhexylamine (373.18 mg, 2.89 mmol), and distilled ethanol (20 mL). Pale yellow solid, Yield: 73%.

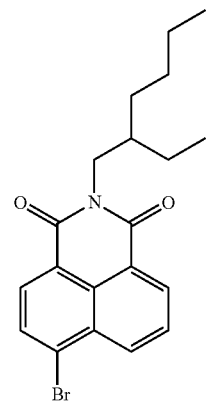 [SMILES: CCCCC(CC)CN1C(=O)c2cccc3c(Br)ccc(c23)C1=O]

$^1$H NMR (400 MHz, CDCl$_3$), δ (TMS, ppm): 8.66 (d, J=7.25, 1H), 8.57 (d, J=8.39, 1H), 8.41 (d, J=8.01, 1H), 8.04 (d, J=7.63, 1H), 7.86 (t, J=7.63, 1H), 4.13 (m, 2H), 1.94 (m, 1H), 1.38 (m, 4H), 1.31 (m, 4H), 0.94 (t, J=7.25, 3H), 0.88 (t, J=6.87, 3H); $^{13}$C NMR (100 MHz, CDCl$_3$), δ (TMS, ppm): 163.76, 132.90, 131.81, 131.02, 130.85, 130.39, 129.88, 128.83, 127.83, 122.94, 122.08, 44.03, 37.66, 30.49, 28.44, 23.82, 22.80, 13.81, 10.38; FTIR ($v_{max}$ in cm$^{-1}$): 3022.32, 2961.79, 2930.47, 2866.60, 1701.70, 1660.08, 1584.35, 1512.26, 1434.13, 1349.22, 1217.03, 1089.61, 1038.46, 927.78, 851.85, 767.30, 668.87; MALDI-TOF: Calculated: 387.0834, found: 387.9449.

Example 6: Synthesis of 6-bromo-2-(tricosan-2-yl)-H-benzo[de]isoquinoline-1,3(2H)-dione (1e)

A mixture of 6-bromo-1H,3H-benzo[de]isochromene-1,3-dione (500 mg, 1.80 mmol), pentacosan-13-amine (919.39 mg, 2.71 mmol), and ethylene glycol (20 mL) was taken in an RB flask and heated at 160° C. under argon atmosphere for 8 hr. After cooling to 30° C., the solid that precipitated was filtered and washed with water. Solvent was removed by vacuum to get pure pale yellow solid Yield: 77%.

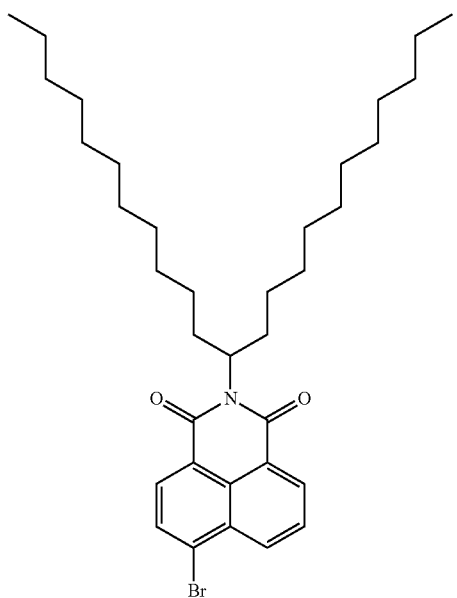 [SMILES: CCCCCCCCCCCC(CCCCCCCCCCC)N1C(=O)c2cccc3c(Br)ccc(c23)C1=O]

$^1$H NMR (400 MHz, CDCl$_3$), δ (TMS, ppm): 8.63 (s, 1H), 8.53 (d, J=8.55, 1H), 8.39 (s, 1H), 8.03 (d, J=7.93, 1H), 7.84 (t, J=7.93, 1H), 5.15 (m, 1H), 2.20 (m, 2H), 1.83 (m, 2H), 1.19 (s, 36H), 0.86 (t, J=6.71, 6H); $^{13}$C NMR (100 MHz, CDCl$_3$), δ (TMS, ppm): 164.78, 163.66, 132.83, 132.37, 131.60, 131.01, 130.85, 130.49, 129.81, 129.17, 128.02, 54.92, 54.62, 42.79, 33.91, 32.30, 31.87, 29.66, 29.56, 29.48, 29.29, 26.87, 22.64, 14.08.

FTIR ($v_{max}$ in cm$^{-1}$): 3021.63, 2927.06, 2856.68, 1701.26, 1658.34, 1583.49, 1512.24, 1461.03, 1403.56, 1349.37, 1216.26, 1043.33, 928.62, 855.00, 762.14, 669.10; MALDI-TOF: Calculated: 597.3181, found: 598.2955.

ADVANTAGES OF THE INVENTION

First report of easy processable liquid organic phosphorescence molecule at 20-30° C.
Phosphorescence in the presence of air at 20-30° C. in a new organic phosphor functional solvent-free liquid is obtained.
Compounds of the present invention exhibit temperature dependent tunable emission features in solution as well as thin films.
Fluorescence based visual low temperature thermometer to detect RT to 77K by fluorescence colour changes is introduced.

We claim:
1. A compound of formula 1(e)

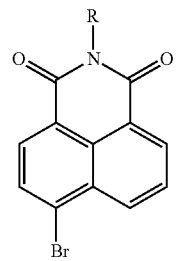

Formula 1(e)

[6-bromo-2-(tricosan-12-yl)-1H-benzo[de]isoquinoline-1,3(2H)-dione]
wherein R=

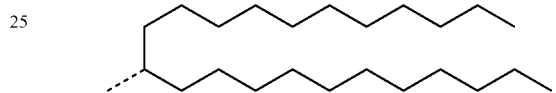

wherein the compound is a pure, pale yellow solid.

2. The compound as claimed in claim 1, wherein the compound exhibits liquid state phosphorescence at 20-30° C. in air.

3. A process for the preparation of a compound of formula 1(e)

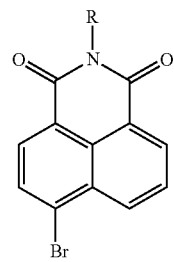

comprising the steps of:
i) charging compound 6-bromo-1H,3H-benzo[de]isochromene-1,3-dione of formula 1, pentacosan-13-amine in alcohol solvent to obtain a reaction mass;

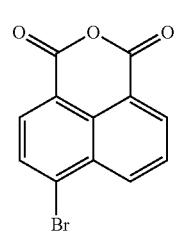

Formula 1 ii) heating the reaction mass as obtained in step (i) at a temperature in the range of 70-160° C. followed by maintaining the reaction mixture at 70-160° C. for a period in the range of 8-15 hr under argon atmosphere to obtain a reaction mass;

iii) cooling the reaction mass as obtained in step (ii) at a temperature in the range of 20-30° C. followed by filtering and washing with water to obtain a solid;

iv) drying the solid as obtained in step (iii) under vacuum to afford the compound of formula (1e) as a pure, pale yellow solid.

4. The process as claimed in claim 3, wherein the reaction mixture is maintained at 160° C. for a period of 8 hr.

5. The process as claimed in claim 4, wherein the alcohol solvent is selected from the group consisting of methanol, ethanol, isopropyl alcohol, n-propanol, n-butanol, ethylene glycol and mixtures thereof.

6. A paintable formulation exhibiting phosphorescence at 20-30° C. in neat form comprising the compound of formula 1(e) as claimed in claim 1.

7. The paintable formulation as claimed in claim 6, further comprising a doping with carbonyl groups.

8. The paintable formulation as claimed in claim 7, wherein the carbonyl groups are introduced with the compounds benzene-1,3,5-tricarbaldehyde and terephthalaldehyde.

\* \* \* \* \*